United States Patent [19]

Gatts

[11] Patent Number: 5,037,375
[45] Date of Patent: Aug. 6, 1991

[54] INDIVIDUAL ENVIRONMENTAL CONTROL METHOD

[75] Inventor: James D. Gatts, San Jose, Calif.

[73] Assignee: Infant Advantage, Inc., Milpitas, Calif.

[21] Appl. No.: 415,064

[22] Filed: Sep. 29, 1989

[51] Int. Cl.⁵ ............................................. A61G 10/00
[52] U.S. Cl. ...................................... 600/21; 128/898
[58] Field of Search ..................................... 600/21-22; 128/897-898, 33-37; 269/323, 324, 325, 328; 5/931, 60-65, 101, 105-109

[56] References Cited

U.S. PATENT DOCUMENTS

| | | | |
|---|---|---|---|
| 1,943,888 | 1/1934 | Ewald | 5/348 |
| 2,534,471 | 12/1950 | Norheim | 5/61 |
| 2,543,426 | 2/1951 | Terhaar | 128/1 |
| 2,723,660 | 11/1955 | Greenberg | 128/1 |
| 2,869,538 | 1/1959 | Hawk | 128/29 |
| 3,076,451 | 2/1963 | Stoner | 128/1 |
| 3,158,150 | 11/1964 | Croasdaile | 128/1 |
| 3,292,611 | 12/1966 | Belkin | 128/1 |
| 3,453,999 | 7/1969 | Neal | 128/24 |
| 3,809,065 | 5/1974 | Gatts | 128/1 |
| 3,993,042 | 11/1976 | Gatts | 128/1 |
| 4,079,728 | 3/1978 | Gatts | 128/1 |
| 4,783,865 | 11/1988 | Stotler | 5/424 |
| 4,934,997 | 6/1990 | Skakas | 600/26 |
| 4,947,832 | 11/1987 | Blitzer | 128/33 |

FOREIGN PATENT DOCUMENTS

| | | |
|---|---|---|
| 255790 | 11/1962 | Australia . |
| 164040 | 9/1949 | Austria . |
| 49508 | 11/1989 | Fed. Rep. of Germany . |
| 663577 | 12/1951 | United Kingdom . |

OTHER PUBLICATIONS

Evenflo-American Glider, Glider Swing by Evenflo Juvenile Furniture Company, Piqua, OH & Los Angeles—3 pages, Dated: 2/89.
Sleeptight Infant Soother by Sweet Dreems, Inc., Columbus, Ohio Undated-Brochure.
SofTouch—by Med Sentry, 690 El Rancho Road, Santa Barbara, CA 93108, 5 pages, dated 4/1/85.
Operator's Manual—Blair Motion Bassinet—Blair Trading Company, 1985, 28 Linden Place, Red Bank, NJ 07701.

Primary Examiner—Lee S. Cohen
Assistant Examiner—John P. Lacyk
Attorney, Agent, or Firm—A. C. Smith

[57] ABSTRACT

An infant environmental transition system and method provides an infant with a controlled, healthy transition from an intrauterine environment to the extrauterine environment, and includes a housing within which the infant is supported by a soft, form-fitting bed. Environment conditions provided within the housing include simulated motions, sounds and tactile sensations resembling the intrauterine environment. A suspension and drive system controls the degree of movement imparted to the housing and to an infant supported therein. The resulting motion closely approximates the motion experienced by the fetus while the mother is walking. The sound profile simulates intrauterine cardiovascular and gastrointestinal sounds. The system simulates day and night variations in motions and sounds, integrates changes to the environment over time toward the natural extrauterine environment, and may respond to infant activity or other imputs at various intervals.

9 Claims, 22 Drawing Sheets

MOTOR STATE SUBROUTINES
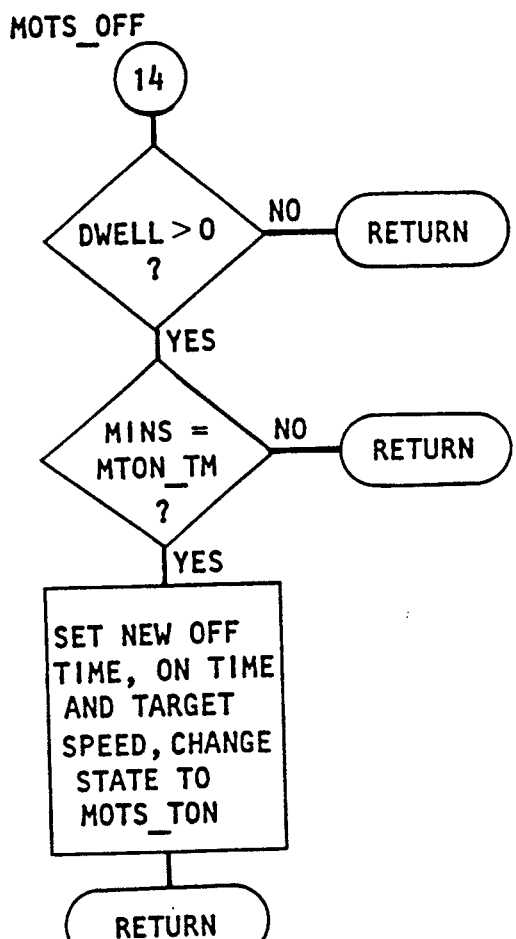
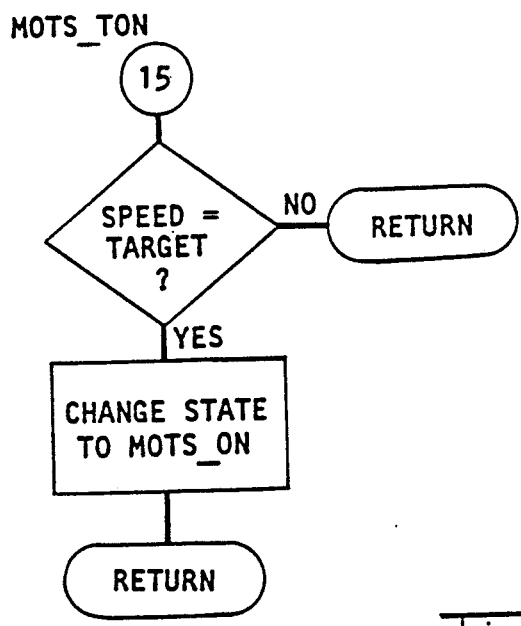
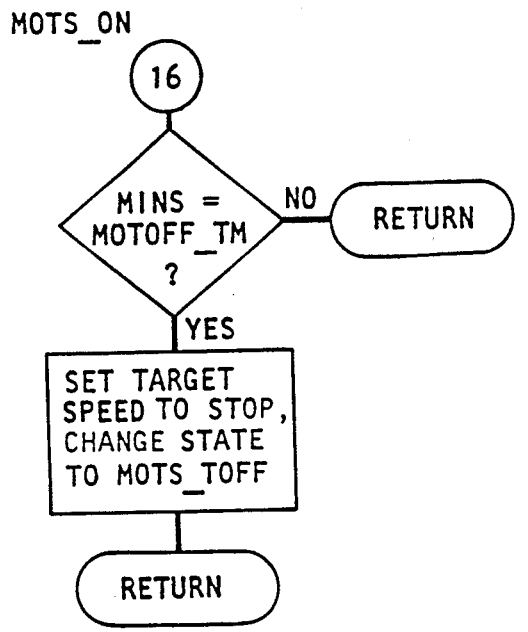
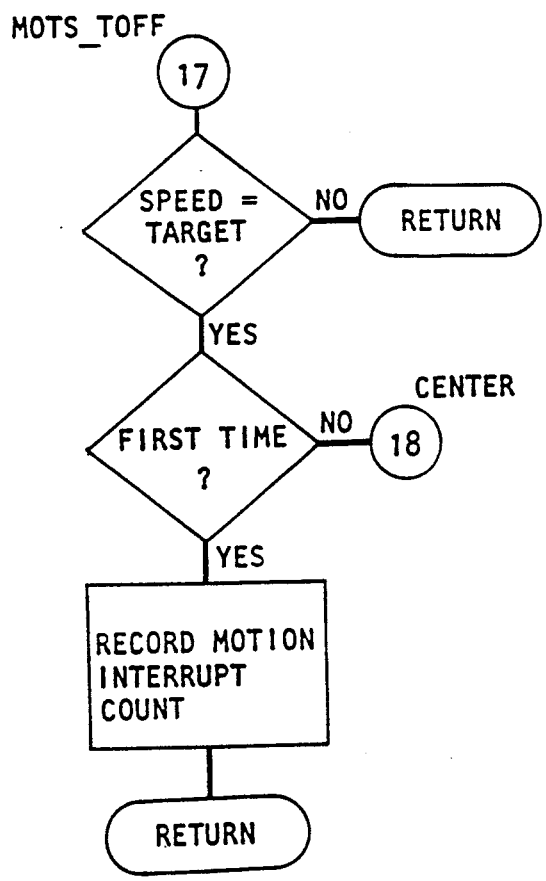
Figure 10F

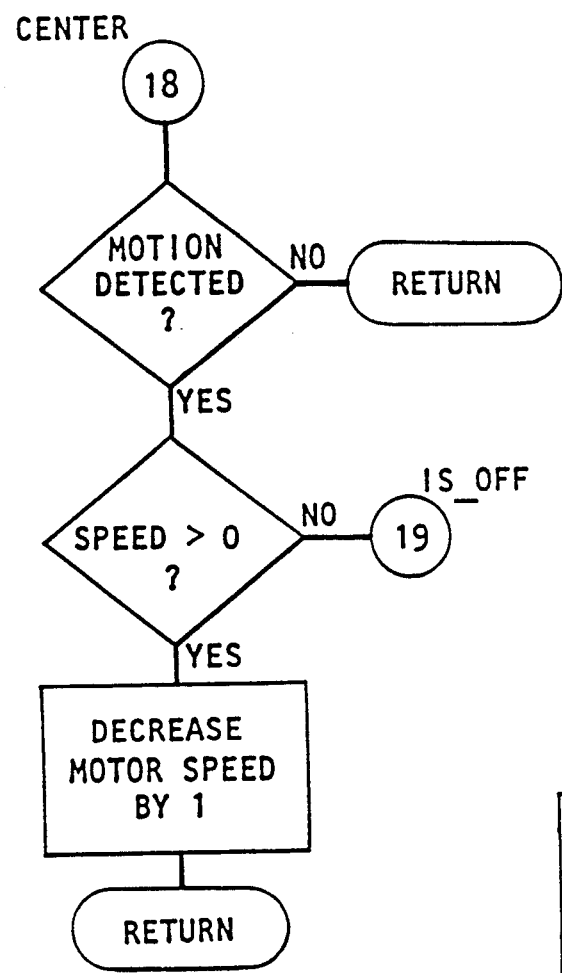
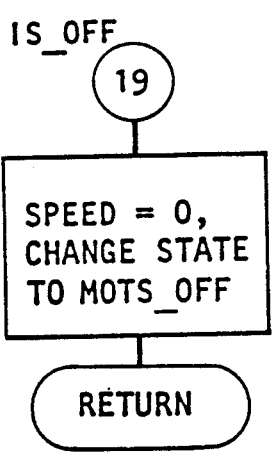
Figure 10 G
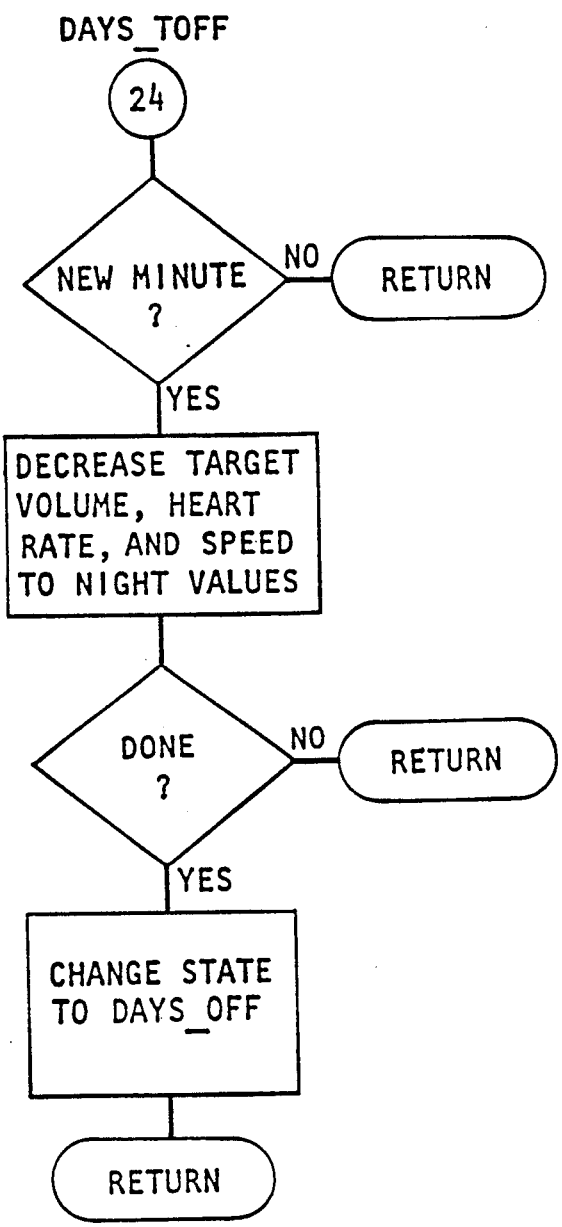
Figure 10 I

DAY/NIGHT STATE SUBROUTINES
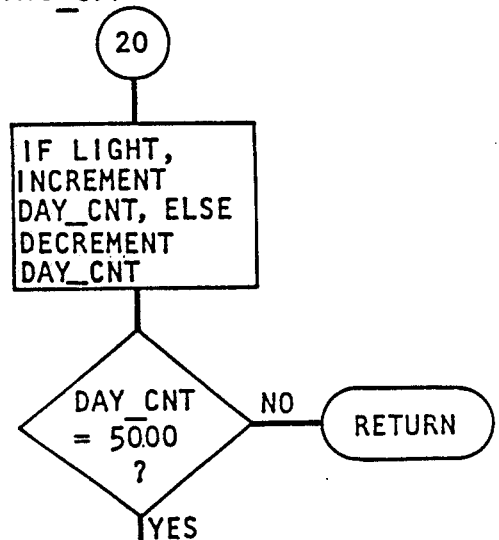
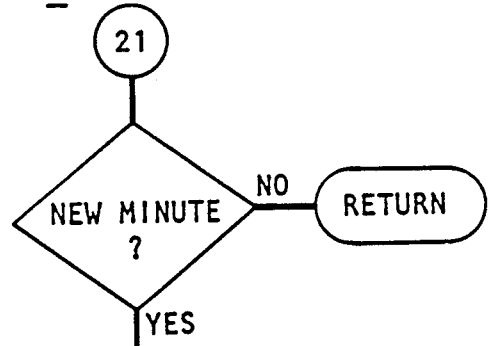
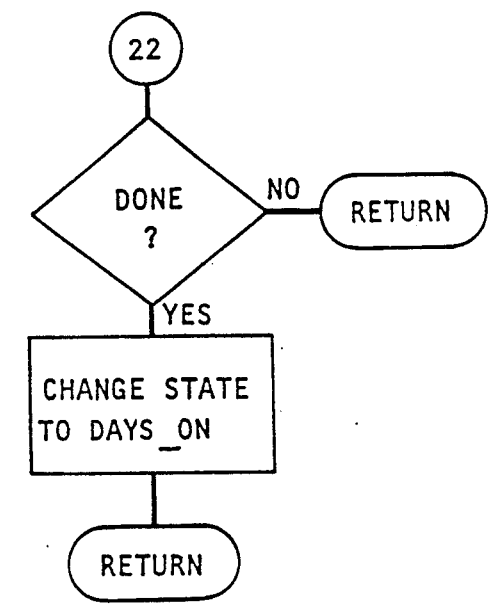
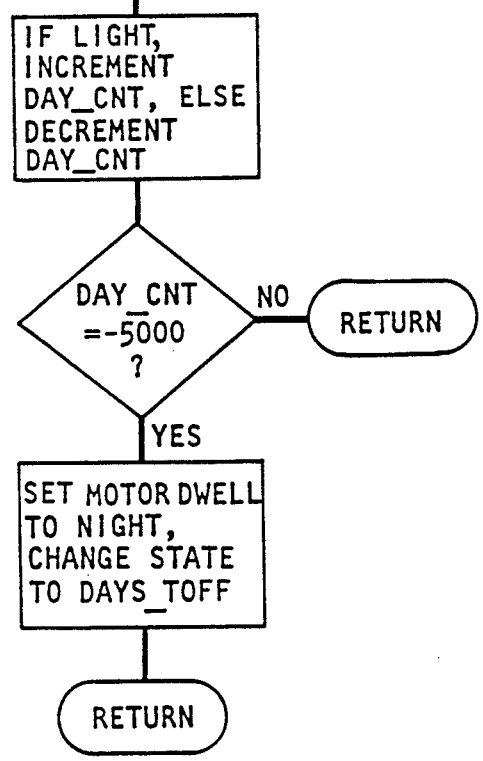
Figure 10H SLOW_STOP & CHECK_MOTOR SUBROUTINES
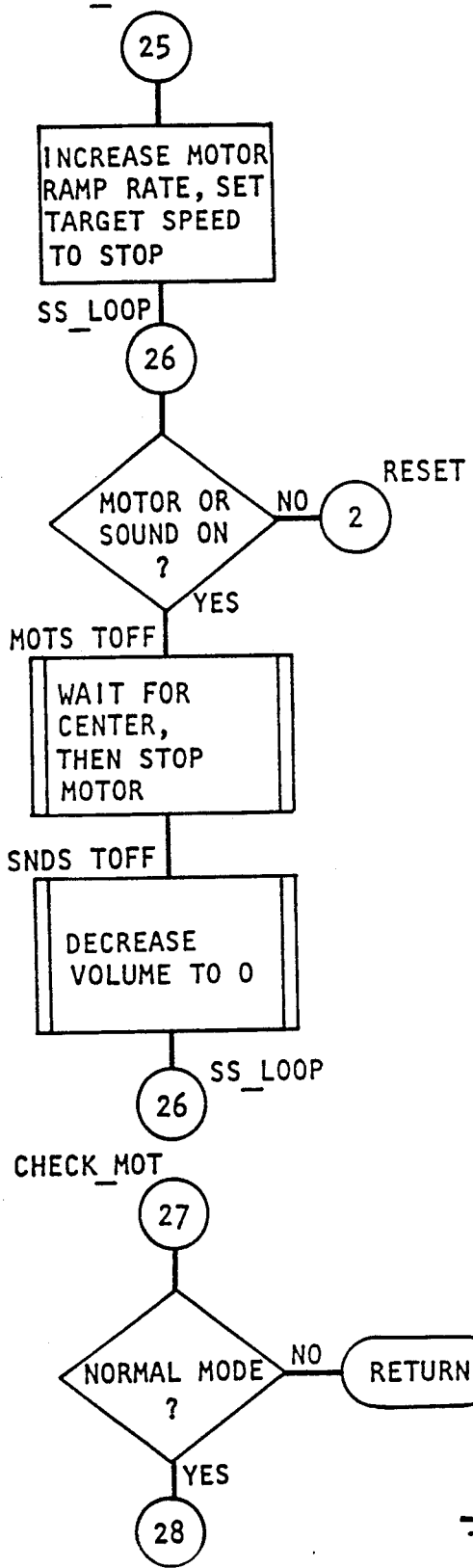
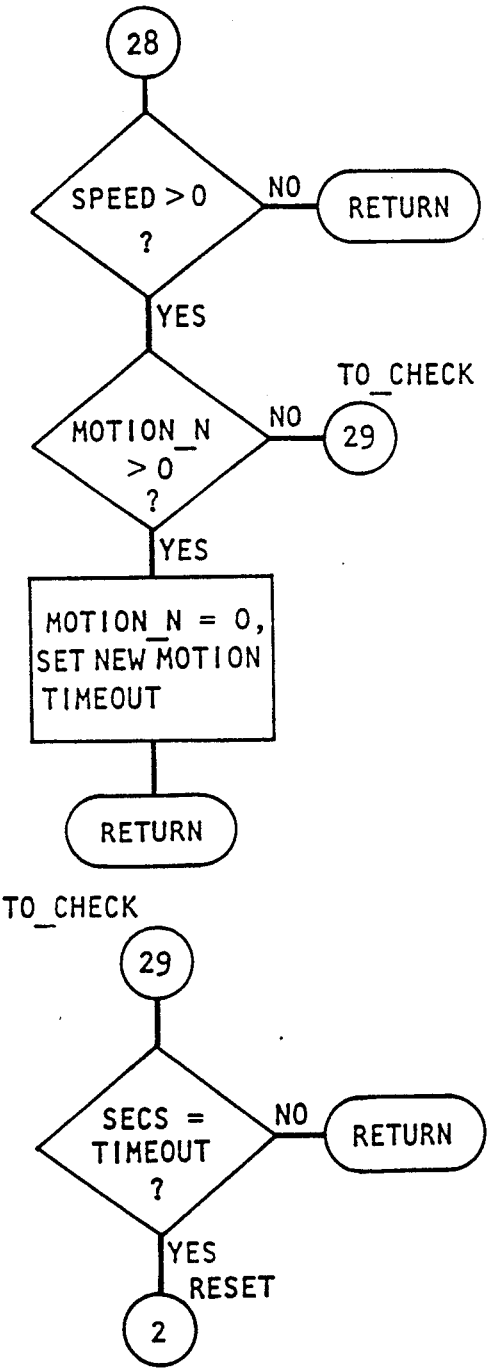
Figure 10J

INDIVIDUAL ENVIRONMENTAL CONTROL METHOD

BACKGROUND OF THE INVENTION

Animals have the ability to adapt to many and varied environmental conditions. The limit of adaptation depends mainly on the animal's absolute physiological limitations and the rate of environmental change or adaptive pressure to which it is subjected.

Perhaps the most difficult transition a mammal is required to make in its lifetime is the change from the intrauterine environment to the extrauterine environment at birth. Every parameter of the infant's environment changes abruptly. Dramatic shifts in temperature, tactile sensation, audio stimuli, motion and light are exacerbated by conditions in the hospital delivery room where most women in modern societies give birth. Even the environment in a loving home is alarmingly unfamiliar, and many infants exhibit prolonged crying and sleeplessness which may be related to transitional stress. It is believed that these abrupt changes in the environment tend to intensify the infant's intrauterine to extrauterine transition and may inflict harm which affects the person's emotional and physical response to adaptive or environmental change throughout the remainder of his or her life. Therefore a gradual and effective transition of the infant from the intrauterine environment to the extrauterine environment may have substantial long-term as well as short-term benefits.

An effective transition system would duplicate as closely as conveniently possible the intrauterine conditions perceived by the infant just prior to birth. It would also provide means for gradually altering environmental stimuli over time until they reflected the natural extrauterine environment.

The environmental stimuli vary in complexity and ease of simulation or control. Light and temperatures are relatively easy to simulate and vary. The sound parameter, while complex in nature, may be generated and controlled by standard means. The motion parameter, however, is quite distinctive. FIG. 1 shows the characteristic pelvic displacement patterns of pregnant women while walking. Duplicating the linear and rotational components of these motions is difficult and requires a sophisticated suspension and motion control and drive system.

U.S. Pat. No. 4,079,728 discloses a programmable environmental transition system with means to provide and control two or more of the above-mentioned environmental stimuli and to modify them over time from initial values closely approximating what the fetus perceives in the uterus just prior to birth to final values typical of the extrauterine environment. Rather than duplicate any particular motion pattern, the system imparts a general rocking motion to the infant, who is suspended therein on a net-like sling.

SUMMARY OF THE INVENTION

The present invention incorporates a motion-oriented environment including a suspension and motion control and drive system which very closely replicates the intrauterine motion the fetus experiences as the mother is walking. A micro-processor integrates desired changes in motion and other stimuli to gradually transition the infant from the simulated intrauterine environment to the extrauterine environment, and to provide wide-ranging system flexibility.

Previous suspension systems commonly generated relatively simple patterns of motion. They also exhibited undesirable axial and radial play which increased over time, suffered excessive wear (causing debris and requiring lubrication and maintenance), and produced unacceptable levels of noise. Previous systems also created simple intrauterine sound parameters that were variable in volume and operating on-time.

The present system overcomes these significant deficiencies and produces a complex, more natural motion which is completely quiet, smooth and continous, with minimal or no friction, high safety and reliability, and low maintenance. In addition, the present invention automatically varies environmental parameters to simulate normal changes in daily maternal activity including varying the operating on-time and volume and rate of sound impulses similar to such parameters as would be found in the biological environment, thus providing the infant with an even more familiar and comforting environment. A baseline cyclic rhythm pattern is established for day and another similar pattern is established for night. In addition the impulse frequency (heart rate sounds attenuated through the hydraulic cardiovascular and placental circulation system) vary with the state of movement of the cradle (as would in the intrauterine environment of the mother). Thus, as the complex rocking motion accelerates slowly, the sound impulse rate also increases in a pattern which tracks the random motion pattern through acceleration and deceleration. When the cradle system is not in motion the sound frequency reverts slowly back to its baseline (day or night) cyclic rhythm pattern. This sound production system thus closely follows living biological patterns that are familiar to the infant. A solar sensor (or manual switch), working in conjunction with electronic circuitry, reduces the speed of the motion at night, to simulate the mother sleeping, and may also be used to vary the intensity of the environmental sounds. Finally, the system integrates the above aspects of sound, motion, and day/night variation and reduces such stimuli over time from initial simulation of intrauterine conditions toward natural extrauterine conditions.

DESCRIPTION OF THE ILLUSTRATED EMBODIMENT

Figure 1:
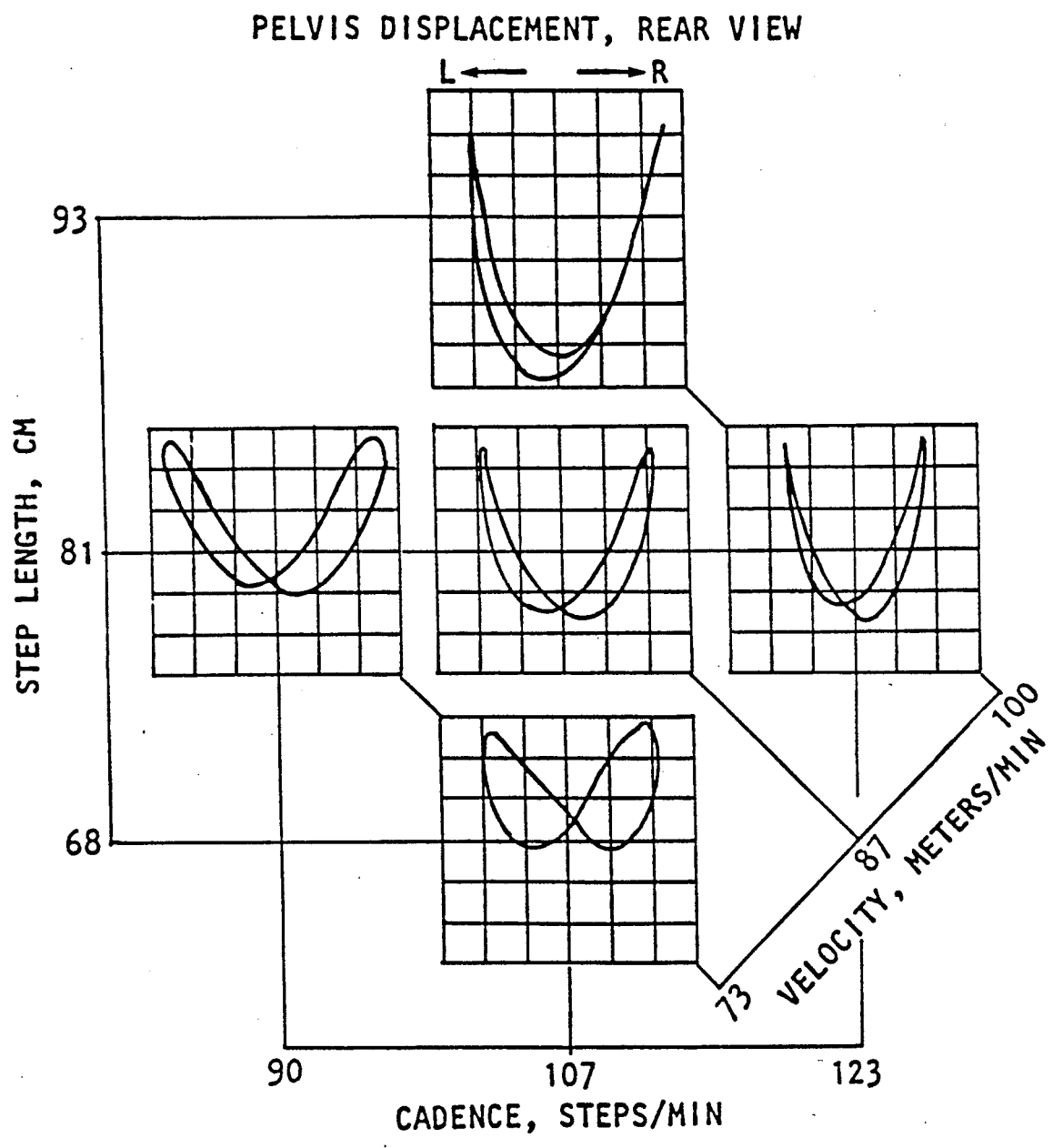
FIG. 1 is a graph showing the characteristic pelvic motion patterns of pregnant women while walking, which patterns are emulated by the motion parameters of the present invention.

Referring now to the drawings and initially to FIGS. 2, 3, 4, 5, 6 and 7, there is illustrated an environmental transition system including suspension and motion control and drive systems, and including a stimulus integration and modulation system, according to the present invention. The system provides for a gradual, controlled transition for the infant by initially simulating its intrauterine environment and gradually transitioning to the extrauterine or everyday environment, thereby reducing adaptive shock and permitting healthy, gradual adaptation. This transition is accomplished by the present system which initially reproduces environmental parameters sensed by the infant just prior to birth. In particular, the system provides and transmits to the infant, via the suspension and motion control and drive systems, a motion which very closely approximates the motion which a fetus experiences as the mother is walking. The system is controlled to vary environmental parameters in a day-night cycle and to reduce stimuli over time until the infant is exposed to parameters which approximate the everyday environment.

The system includes a cradle 1 on a moving platform 30 which is supported for motion along several axes by the suspension system including lower flexure supports 11 and upper flexure supports 3. The cradle 1 includes a soft, form-fitting mattress 33 on which the infant rests, and includes bolsters 31 with bolster straps 32 to simulate the confining intrauterine tactile environment.

The system further includes a sound transducer 2 disposed in the cradle 1 beneath the level of the infant positioned therein on mattress 33. The sound transducer 2 may include one or more signal sources connected thereto such as a phonograph, tape player, electronic signal generator, or similar controllable sound generating device. The sound profile generated thereby may comprise a variety of different simulated sounds or actual recordings of the noises present in the near-term pregnant uterus. It may also comprise other sounds such as music or house sounds which may be generated electronically, recorded on tape, or played from a transmitter and reproduced via a receiver as a signal source in the cradle 1. The sounds are reproduced from the transducer or speaker 2, which is suitably mounted below the mattress 33. The sound directed to the infant, like other environmental factors, may be gradually changed over a period of a few months from intrauterine sounds to sounds typical of the outside world.

The cradle 1 is supported by a suspension system which includes four thin rectangular lower flexures 11 that are formed of spring steel, or the like, and that have their lower ends affixed to base 27 via lower mounting brackets 29 and their upper ends affixed to the moving platform 30 via upper mounting brackets 29. This specific design enables the platform 30 to undergo essentially linear motion along the longitudinal axis of the cradle 1 while keeping the moving platform 30 parallel to base 27 and constrained against lateral movement. As platform 30 moves relative to base 27, the lower flexures 11 bend as shown by broken lines 39.

Figure 3:
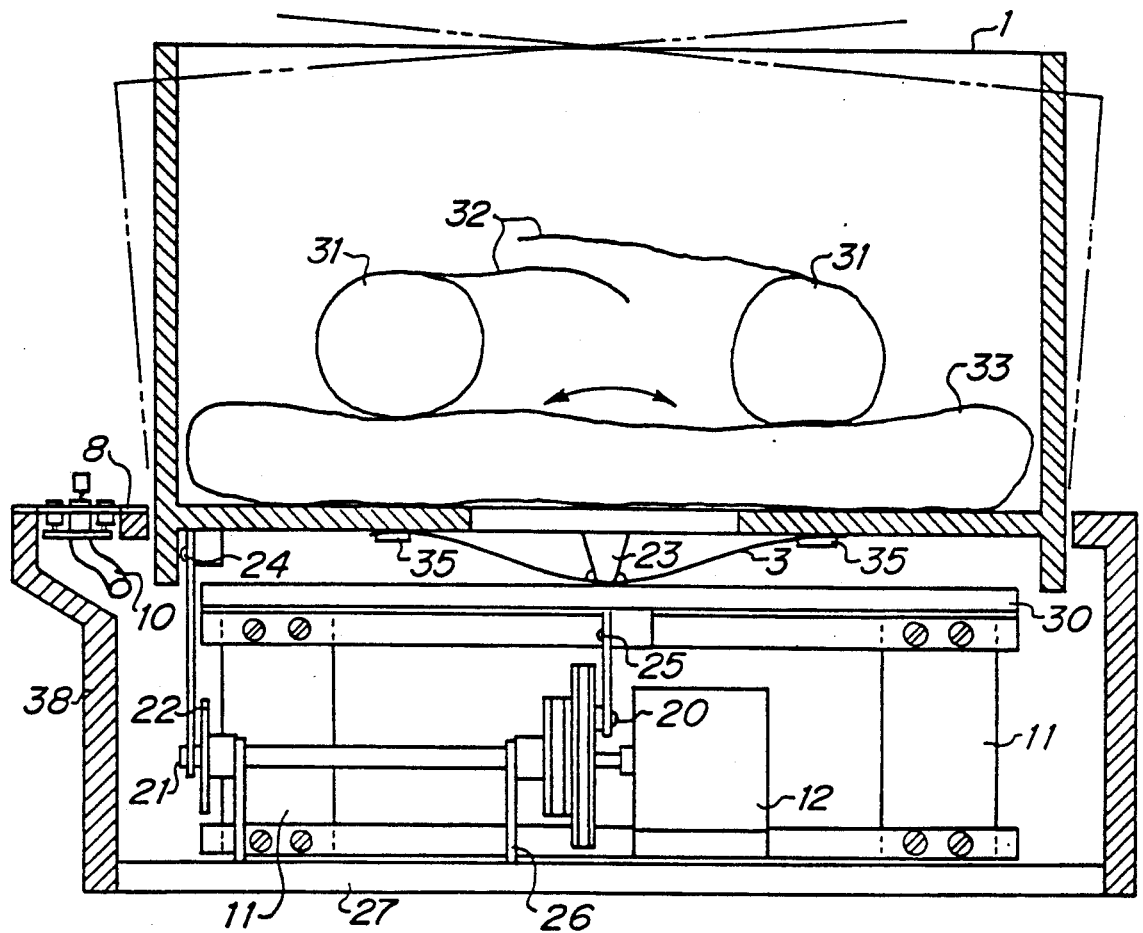
FIG. 3 is an end view of the simulator of FIG. 2.
Figure 6:
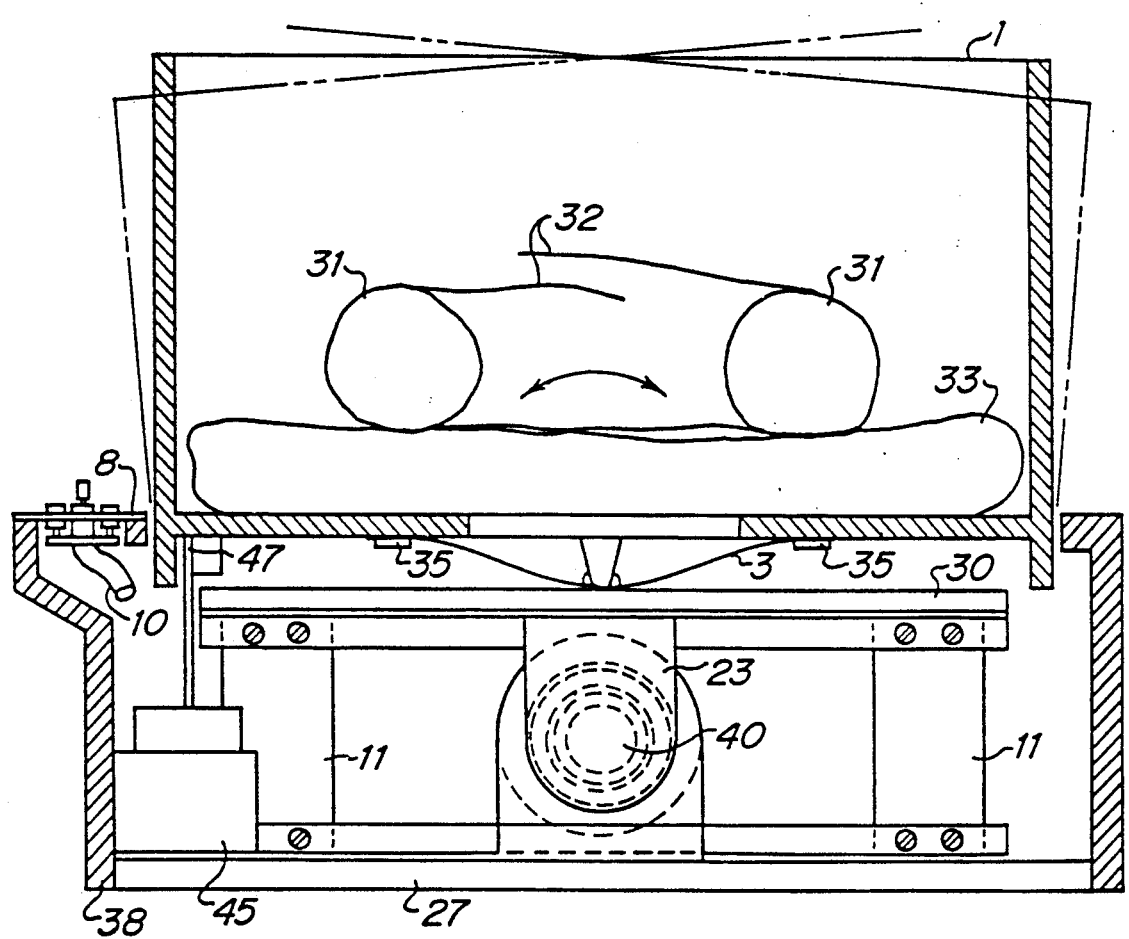
FIG. 6 is an end view of the simulator of FIG. 5.

The platform 30 supports and carries the cradle 1 via the upper flexures 3 and associated parts as described below. The upper flexures 3 are formed of thin spring steel, or the like, and are affixed at the center of the moving platform 30 by the clamp plates 34. The ends of the upper flexures 3 are affixed to the bottom of the cradle 1 by the upper clamp plates 35. The cradle 1 is supported by the two cradle pivots 23 which are affixed to the bottom of cradle 1. As shown in FIGS. 3 and 6, these upper flexures 3 and cradle pivots 23 enable the cradle 1 to rotate about the bottom of the cradle pivots 23 while the upper flexures 3 bend as necessary to restrain the cradle 1 against lateral and longitudinal motion on the platform 30. The specific system design and geometry is such that the weight of the moving mass counteracts almost all of the force required to deflect the lower flexures 11. Therefore, the actual force required to move the mass, which includes cradle and infant, is very low. This reduces motor requirements and manufacturing costs and increases the smoothness of the resulting motion.

The characteristic motion of cradle 1, which is comprised of linear and rotational components as shown in FIG. 1, may be generated in accordance with an embodiment described below.

Figure 2:
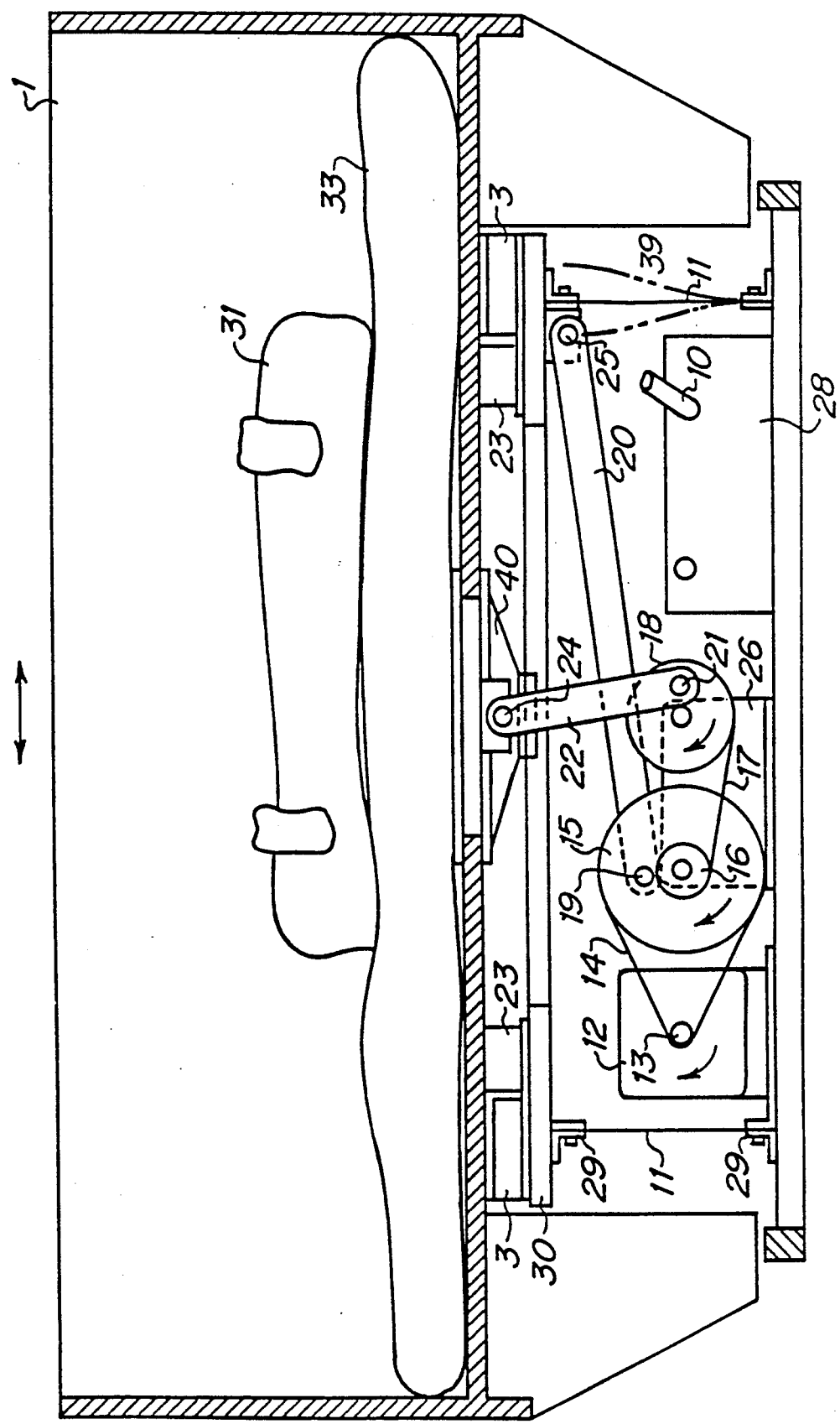
FIG. 2 is a side elevational view of the simulator according to one embodiment of the present invention.
Figure 4:
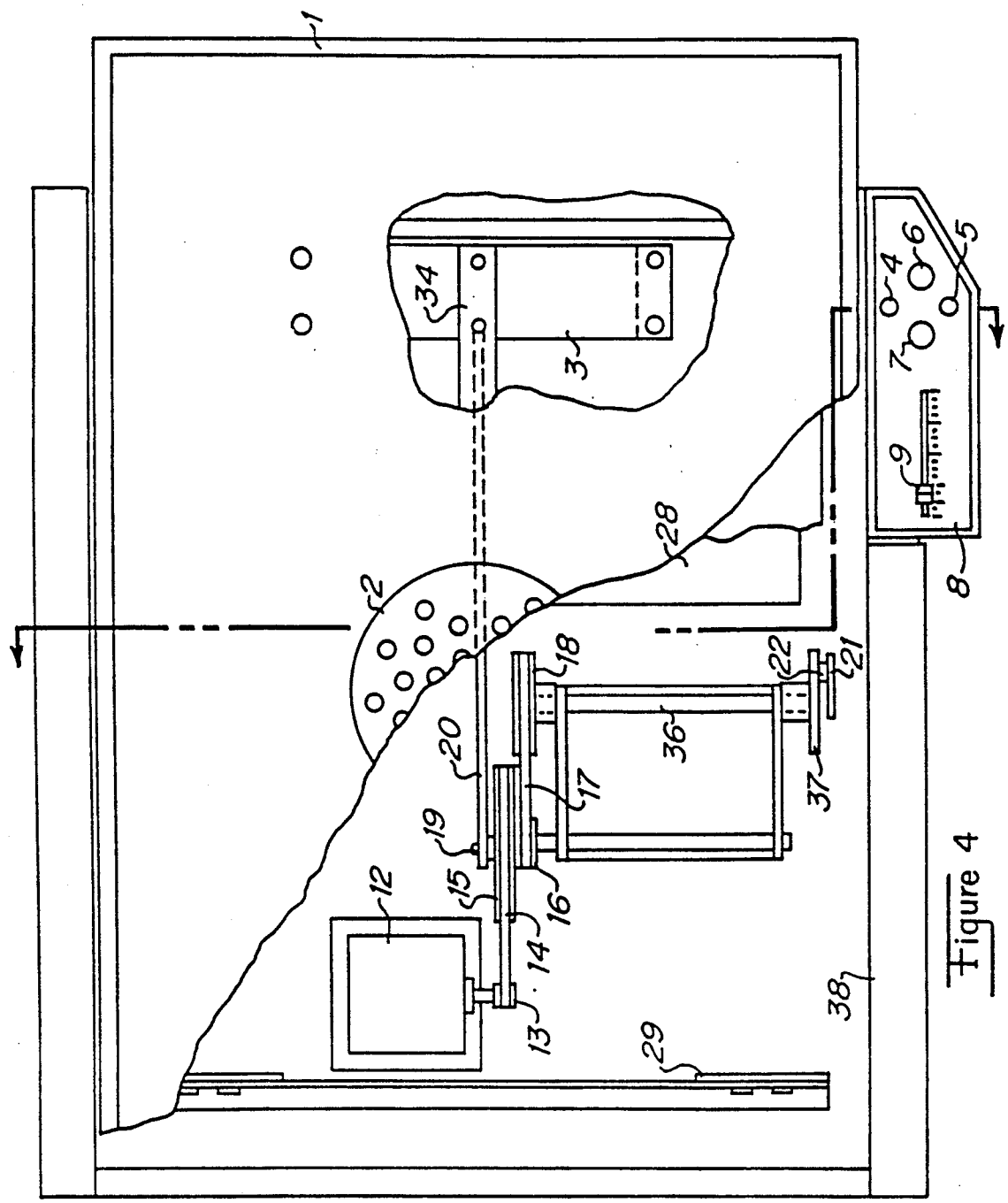
FIG. 4 is a top cutaway view of the simulator of FIG. 2.

With reference to FIGS. 2, 3 and 4, the motion control and drive system for one embodiment of the present invention drives both the linear and angular motions, as shown by the arrows in FIGS. 2 and 3, by means of a low-voltage, alternating-current motor 12 that is controlled by the electronic circuitry in module 28. As a result of the use of low-voltage AC motor 12, no high voltage is required anywhere in this embodiment, for enhanced product safety. Also, the commutator and brushes of D.C. motors are eliminated with concomitant reductions in the possibilities of electrocution, fire or explosion.

Referring now to the linear motion components, motor 12 drives motor pulley 13, which drives primary belt 14, which drives primary driven pulley 15. This primary speed reduction scheme provides the desired oscillation speed of the linear motion of cradle 1. The present design incorporates a 300 RPM motor for a daytime cradle speed of about 30 linear cycles per minute. The magnitude or frequency of drive signal applied to the motor 12 may be altered to provide the desired cradle speed.

Referring again to FIG. 2, linear drive pivot 19, which is on driven pulley 15, is connected to linear drive link 20, which is connected to linear drive pin 25, which is affixed to moving platform 30. As shown in FIG. 2, rotation of linear drive pivot 19 about the center of pulley 15 drives cradle 1 in linear oscillations along the longitudinal axis of the cradle 1. The longitudinal displacement of cradle 1 may be altered by positioning the drive pivot 19 at different radii on the driven pulley 15.

Referring now to the rotational motion components, as shown in FIGS. 2 and 4, secondary drive pulley 16 drives secondary belt 17, which drives secondary driven pulley 18 which is connected to shaft 36, which is connected to drive disk 37. Rotational drive pivot 21 is attached to drive disk 37, which is connected to rotation drive link 22, which is connected to cradle drive pin 24, which is affixed to the bottom of cradle 1. Drive bracket 26 supports and provides the pivots for pulley 15, pulley 18, shaft 36 and drive disk 37. Belts 14 and 17 are used to provide both primary and secondary reductions without significant noise. The degrees of rotation of the cradle 1 relative to platform 30 may be altered by positioning the drive pivot 21 at different radii on drive disk 37.

The ratio between pulley 16 and pulley 18 may be tailored to provide the desired relationship between the linear and rotational motions of cradle 1. The present design utilizes a 2:1 ratio which provides a maximum or daytime cradle rotational motion of about 15 oscillations per minute but, of course, other suitable values may also be used. The combined motion control and drive system of this embodiment produces a linear motion of approximately 1.5 inches and rotational motion of approximately 9.5 degrees. This motion very closely replicates the intrauterine motions experienced by the fetus while the mother is walking, as illustrated in FIG. 1 and as translated 90 degrees from the most common "head down" intrauterine position of the fetus to the position of the infant laying in the cradle 1.

Figure 5:
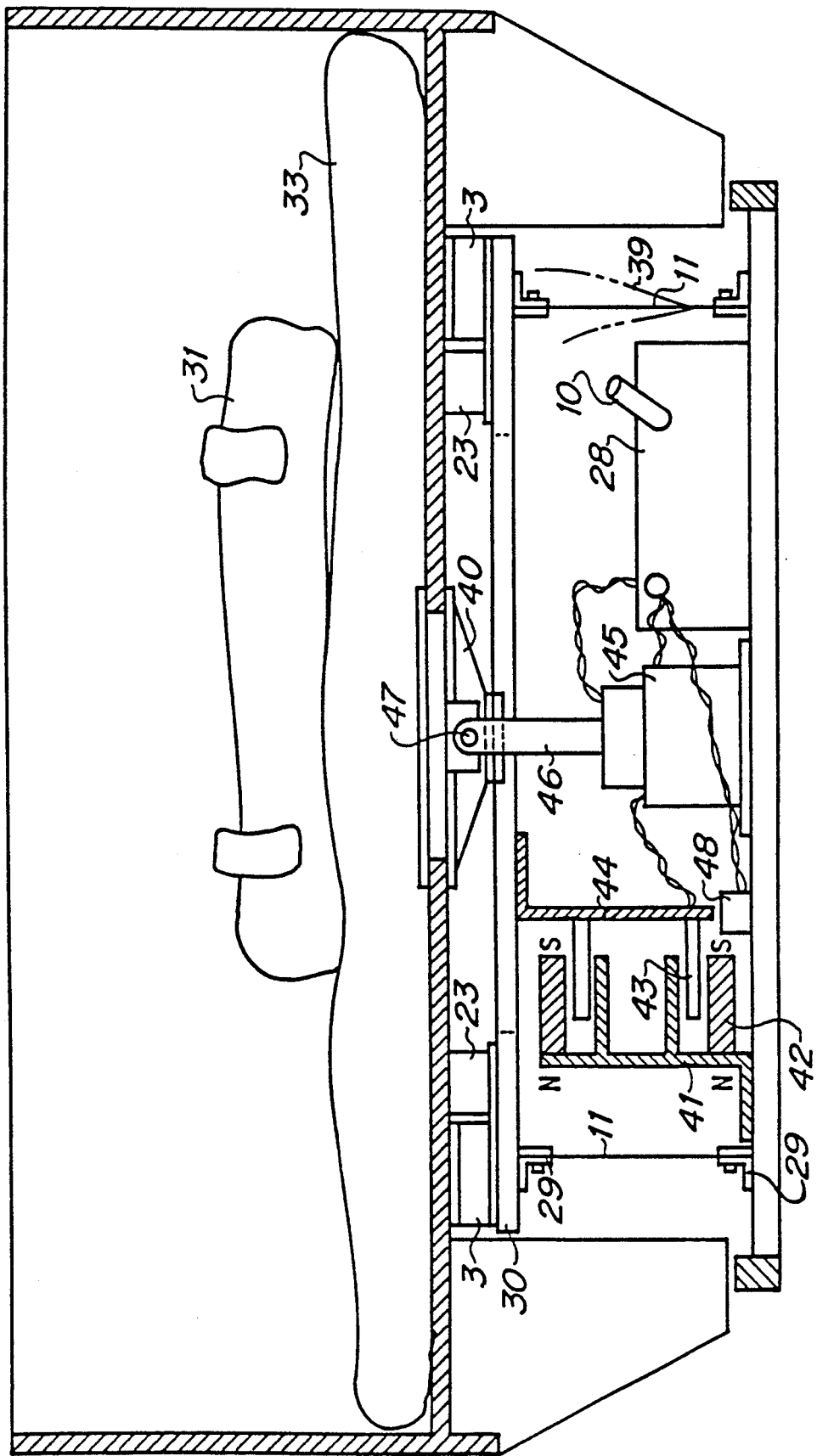
FIG. 5 is a side elevational view of the simulator according to another embodiment of the present invention.
Figure 7:
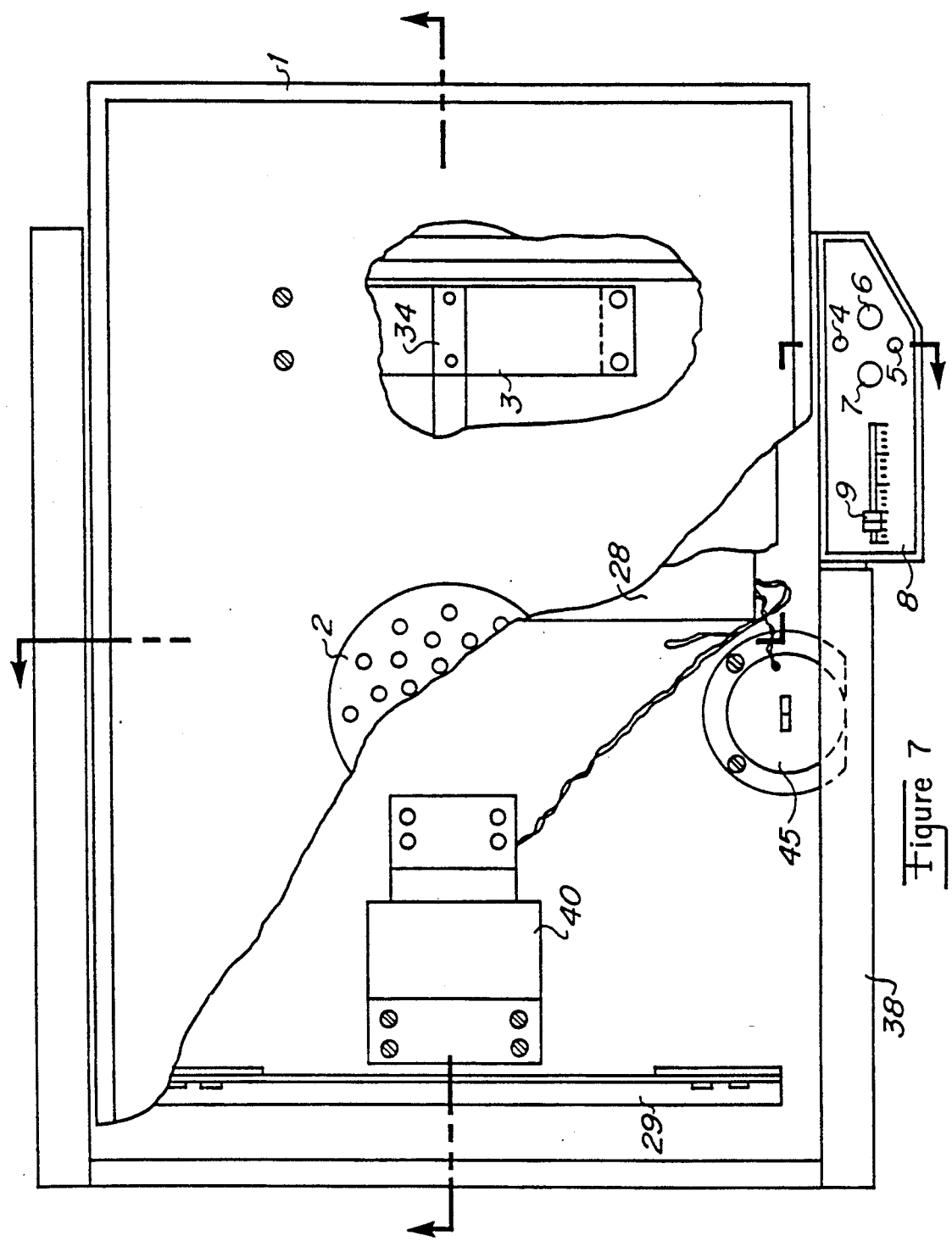
FIG. 7 is a top cutaway view of the simulator of FIG. 5.

With reference to FIGS. 5, 6 and 7, the motion control and drive system in another embodiment of the present invention provides the linear and rotational motions using separate linear activators or motors 41-44 and 45.

The linear motion motor 41-44 consists of a moving coil motor with the moving electromagnet 43 attached to bracket 44 which is attached to moving platform 30. Motor magnet 42 is attached to bracket 41 which is solidly attached to base 27. Magnet 42 may be an electromagnet; however, the present design utilizes a permanent magnet. Magnet 42 is polarized as shown, with bracket 41 having a cylindrical center portion which provides the circular return path for the magnetic flux. Electromagnet 43 is energized and controlled by electronic circuitry in module 28. When electromagnet 43 is energized, the resulting magnetic field causes moving platform 30 to move to the right or left, depending upon the direction of the current flow in the coil, as a result of the magnetic field either attracting or repelling the magnetic field of magnet 42. Motion sensor 48 is provided to detect the motion. Motion sensor 48 may be a simple single stage sensor or a multi-stage device to sense motion, direction of motion, velocity, etc. Such motion sensor 48 may be one of many types of devices such as a simple mechanical switch, optical or magnetic sensor, linear variable differential transformer, encoder, and the like, for connection to the electronic circuitry in module 28 to set motion limits, provide conventional feedback control, or the like.

Control of electromagnet 43 by the electronics module 28, in conjunction with motion sensor 48, allows simple or sophisticated linear motion control of the cradle 1. Cradle 1 motion may be increased or otherwise modified by controlling the current, voltage, duration of pulses or the like, applied to electromagnet 43 in either an "open-" or "closed-loop" type of operation. Also, different phased relationships and different relative speeds of translational and rotational motions of the cradle 1 may be implemented under control of independent signals supplied to the two linear motion motors from the electronic circuitry in module 28.

The rotational motion of cradle 1 is driven by rotation motion motor 45 which is connected to cradle 1 by rotation drive pin 47 through rotation drive link 46. Motor 45 may be similar to motor 41-44 and works in conjunction with a rotational motion sensor similar to motion sensor 48 (described above), which is not shown. Motor 45 may be driven in either an "open-" or "closed-loop" mode to provide a motion control system.

Motor 41-44 and motor 45 may be controlled completely independently of each other, to provide numerous combinations of linear and rotational motions of cradle 1. As a result, in addition to replicating the motion the fetus experiences within the uterus while the mother walks, the system can also simulate and transition between many other types of motion the fetus perceives during pregnancy. For example, the system can simulate motion perceived while the mother sleeps, and can then vary motion amplitudes and phase relationships of linear and rotational motions to more closely approximate the motion perceived while the mother is walking. The controlled transitions are silent and smooth, such as by 'ramping' up or down between operating conditions over several minutes, so as not to stress or awaken the infant.

Figure 8:
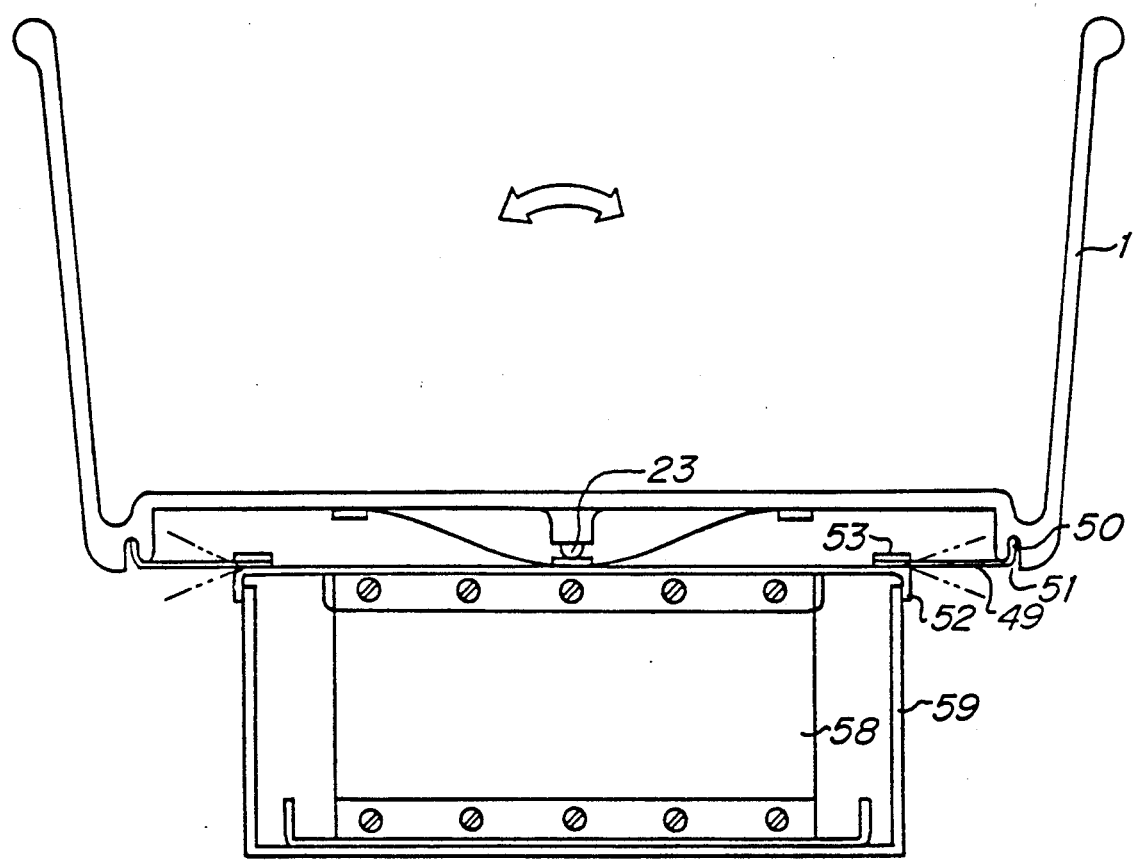
FIG. 8 is a cross-sectional end view of still another embodiment of the present invention, including wide flexures and flat membrane safety features.

FIG. 8 shows an alternate embodiment of the suspension system of the present invention. In this embodiment, two wide flexures 58 replace the four narrow lower flexures 11 shown in FIGS. 2, 3, 5 and 6. Wide flexures 58 are attached to moving platform 52, which supports cradle 1, which rotates substantially about cradle pivot 23. Flat membrane 49 is attached to moving platform 52 by membrane clamping plate 53. The outer end of flat membrane 49 is securely fastened to cradle 1 by membrane retainer 50 which is press fit into membrane groove 51 in cradle 1 to inhibit anyone or anything from being pinched or trapped between moving cradle 1 and moving platform 52. As shown by the phantom lines in FIG. 8, the rocking rotational motion of cradle 1 causes flat membrane 49 to experience only a small amount of stretching, less than 6 percent, because of the specific geometry that places the flat membrane 49 on the horizontal axis of the cradle 1 pivot point. As a result, flat membrane 49 stretch is limited to the difference between the radius swung by the outer end attached to cradle 1 and the radius swung from the innermost end of flat membrane 49. Minimizing stretch of the membrane promotes long life and makes it possible to use low-cost, flat elastomeric materials for membrane 49.

Figure 9:
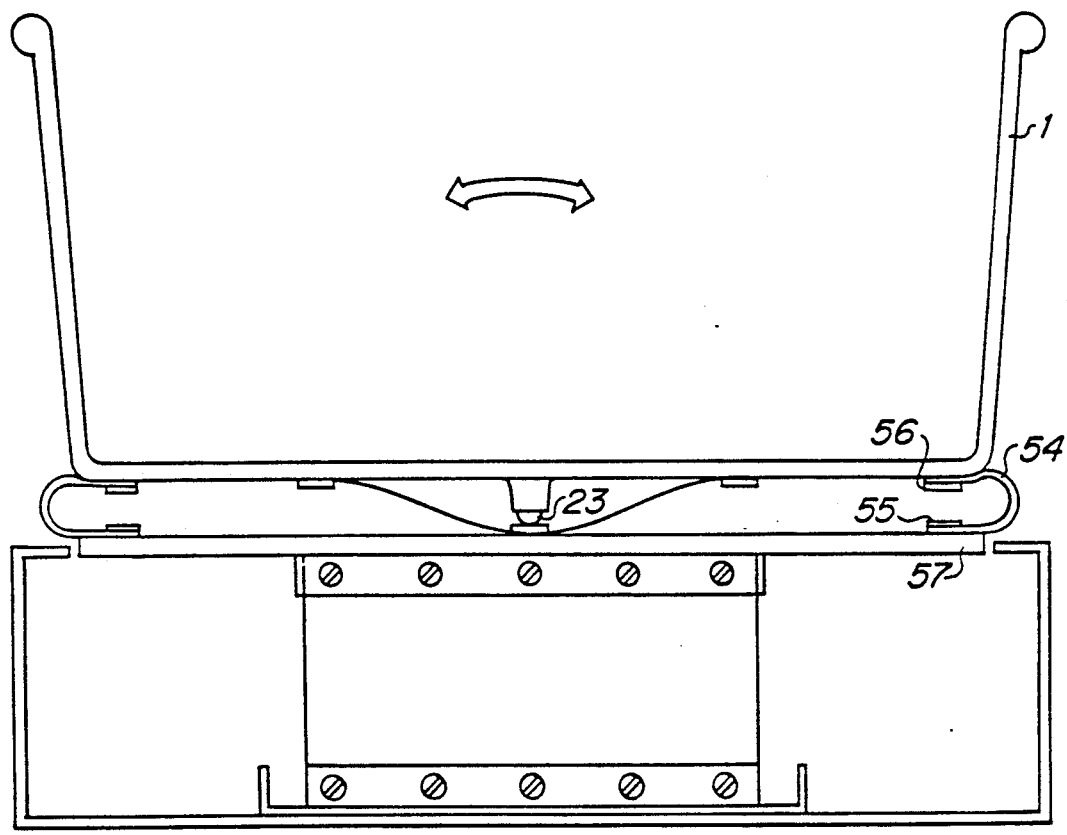
FIG. 9 is a cross-sectional end view of still another embodiment of the present invention, including wide flexures and curved membrane safety features.

FIG. 9 shows an alternate embodiment of the safety mechanism of the present invention. This embodiment utilizes a curved membrane 54, which is attached to cradle 1 by upper clamp plate 56 and to moving platform 57 by lower clamp plate 55. The rocking rotation of cradle 1 causes curved membrane 54 to be opened and closed. Resultant stresses are distributed over the long length of curved membrane 54, to promote long life of the membrane. The design of curved membrane 54 inhibits anyone or anything from being pinched or trapped between moving cradle 1 and moving platform 57 to enhance the safety of the present invention.

The system described above automatically varies the environmental stimuli of the cradle in a day-night cycle to simulate the mother's activities while awake or sleeping. This is accomplished by solar sensor 4 working in conjunction with the electronic circuitry in module 28 in the manner shown in FIGS. 10(a)-(m). The solar sensor 4 detects reduced ambient light and switches to the "nighttime" program of motion and sound. Of course, such day or night operating programs may also be implemented under control of a timer or manual switch. The present invention utilizes a night speed of about 50–60% of the day speed, but other ratios may, of course, also be used. Alternatively, individual actuators coupled to the platform 30 and to the cradle 1 may impart independent motions along the selected axes of motion in daytime and nighttime operations under control of the electronic circuitry in module 28. And, the present invention supplies sound volume during night operation that is approximately 85–90% of the day volume, but other ratios, of course, may also be used.

The integration of various previously-described aspects of motion and sound generation, day and night variations, and infant age-dependent reduction of stimuli over time, from initial intrauterine values to natural extrauterine values, is accomplished under control of the electronic circuitry in module 28, as shown in FIGS. 10(a)–(m) and 12. In one embodiment, a microprocessor may receive inputs from the stop/reset switch 6, start switch 7, age-control slide potentiometer 9, solar sensor 4, and motion sensor such as a switch comprising a photodiode/photosensor pair (not shown). The microprocessor generates outputs which control sound generation through speaker or transducer 2, and which control the speeds of motor 12 or motors 41–44 and 45 (depending on the embodiment), the status of indicator lamp 5, and the function of a timer.

Figure 10A:
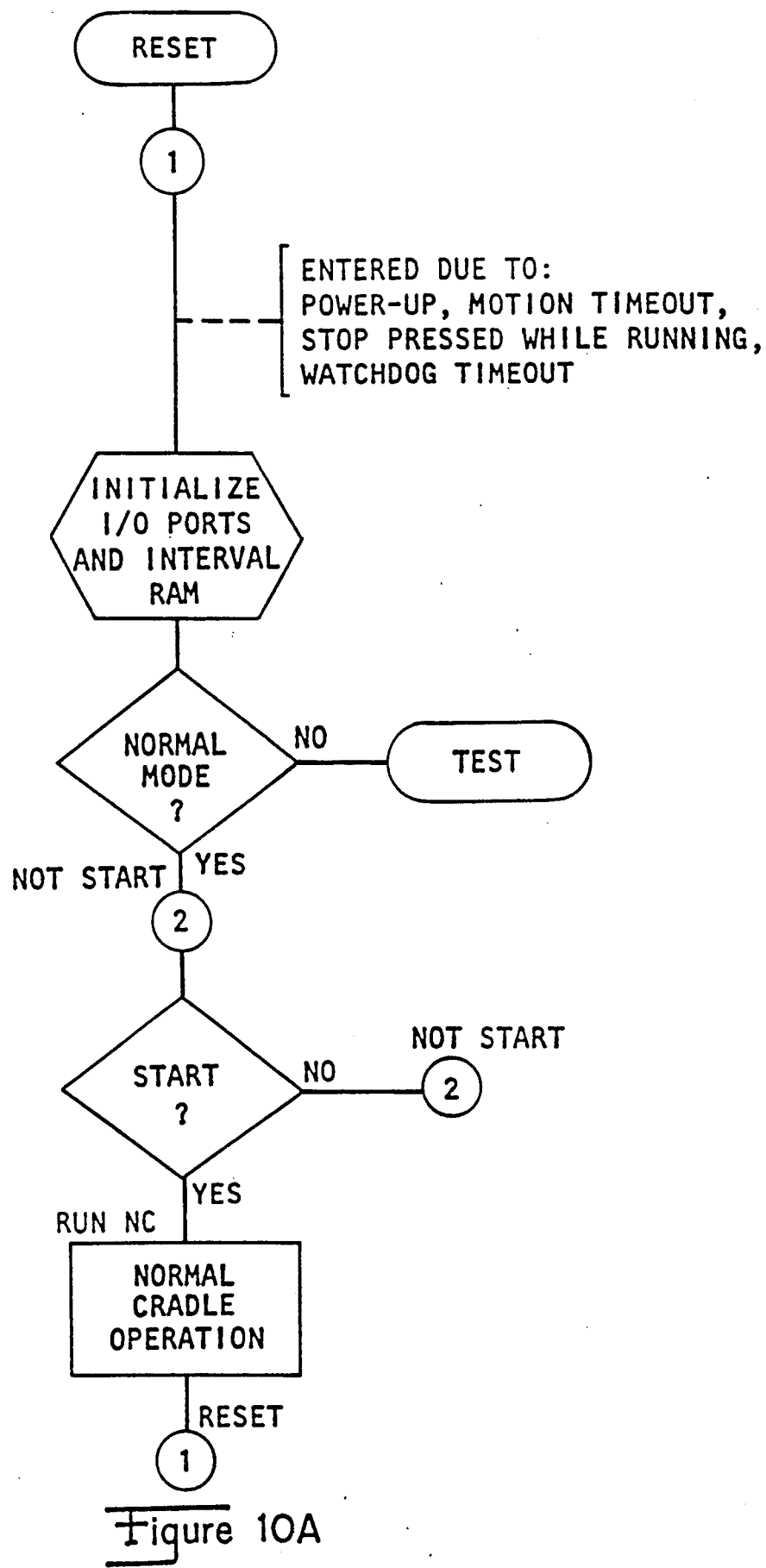
FIGS. 10 (a)–(m) form a flow chart of the electronic control system of the present invention.

Considering the electronics control scheme in greater detail, and with reference first to FIG. 10(a), the program begins with Reset upon power-up or motion time out. Also, if the stop/reset switch 6 is pressed, the program will go to Reset once the sound and motor are off. A timer, when it times out, causes the cycle of operation to begin again. The controlling program initializes the microprocessor and its internal RAM to begin operation. The program checks the test switches to see if a test mode has been selected. If yes, a test routine is exercised. If no, the start switch 7 must then be pressed. Once start switch 7 is pressed, the main sequence for normal operation of the cradle is exercised.

Figure 10B:
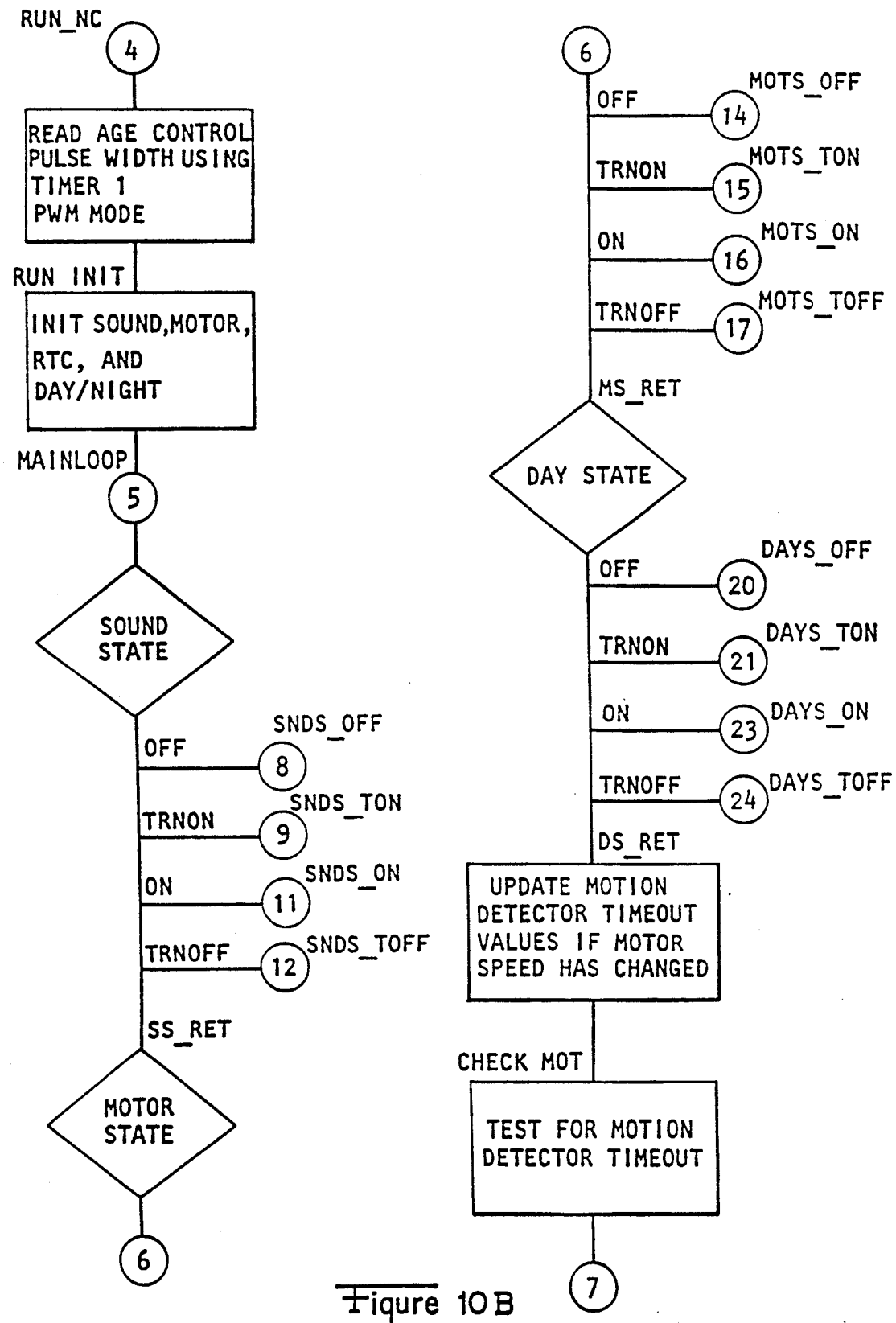
Figure 10C:
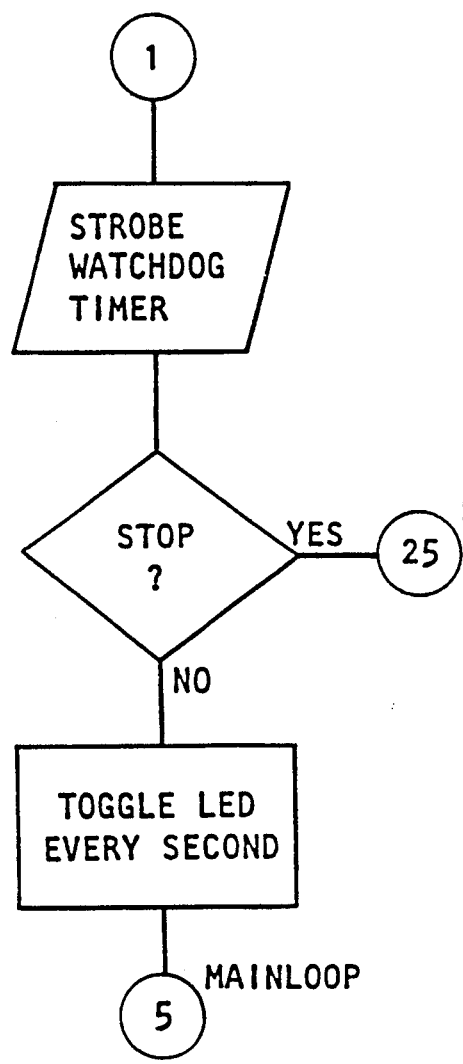
Figure 10E:
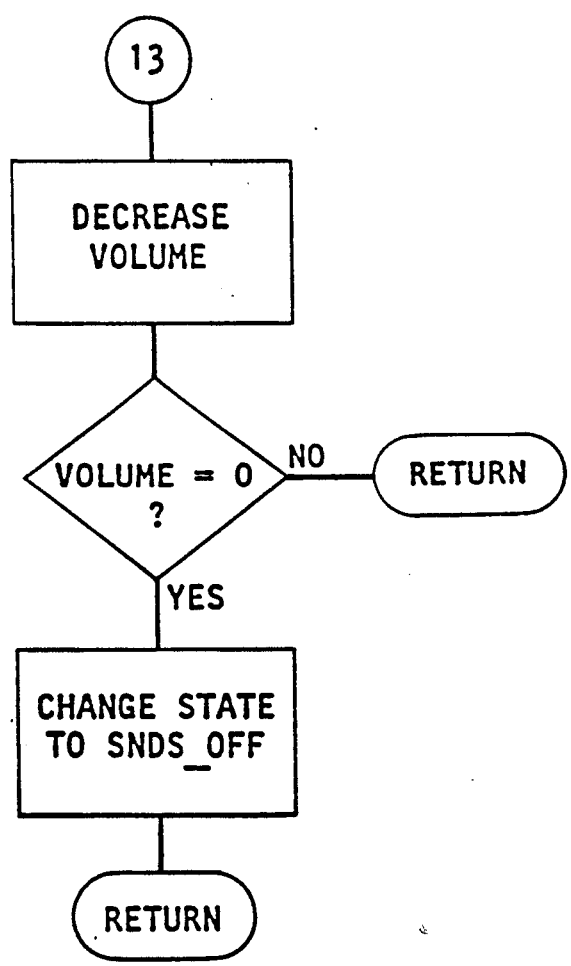
Figure 10D:
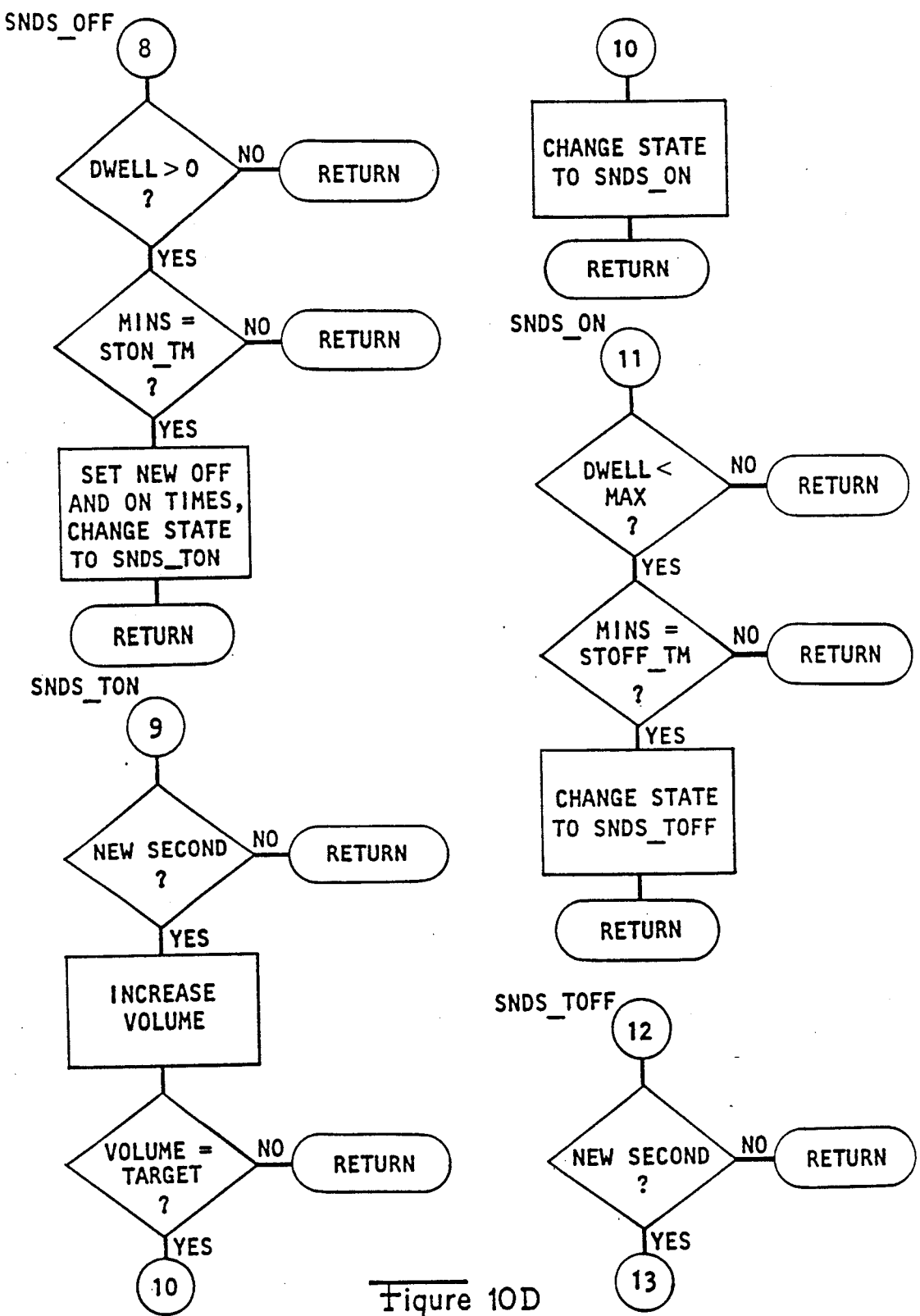

Referring now to FIGS. 10(b)–(c), the program senses the age-control pulse-width from age-control potentiometer 9 and generates a number between 0 and 255 corresponding to the age setting. Then, the sound, motor, and day-night state processors are initialized. Depending on the state of the cradle, each processor executes one of its four functions. For example, considering the sound-state processor, the sound will be either off, turning on, on, or turning off, and the processor will execute the corresponding subroutine, as shown in FIGS. 10(d)–(e). Similarly, the motor will be either off, turning on, on, or turning off, and the appropriate subroutine will be executed, as shown in FIGS. 10(f)–(g). For the day-night state processor, the four states are day off (which means it is night), day turning on (which means night is becoming day), day on (which means it is day) or day turning off (which means day is becoming night), as illustrated in FIGS. 10(h)–(i).

The turn on and turn off functions execute the gradual ramping up or down of the sound level, motor speed, and day-night transitions. The sound on-off and motor on-off ramping operations are much faster than the day-night transitions, which take about five minutes.

While the cradle is in normal operation, the microprocessor continuously executes the main control program. After executing the appropriate sound state, motor state, or day-night state, the system updates the motion-detector time-out values every time the motor speed changes, and then seeks a motion-detector time out. As shown in FIG. 10(c), the main control program also strobes the timer, scans stop/reset switch 6 for indications of a need to shut down and, if necessary, toggles indicator lamp 5 once every second.

Referring now to FIGS. 10(d)–(e), the present invention executes one of four sound-state subroutines, depending on the state of the sound, as indicated by the dwell. Dwell is the amount of time the sound is on, expressed either as a percent or as a number between 0 and 255, where 255 represents 100%, 128 represents 50%, and so on. If dwell equals 0, the sound is off and will never turn on, i.e., the sound-off loop continues to execute each time dwell at 0 is detected (for example, at age equals four months). If dwell is greater than 0, the sound is on part of the time, and the system seeks the appropriate turn-on time.

The turn-on times are set randomly every time the motor is turned on. The first turn-on time is set at Reset/initialization, when the system first executes the main control program. When the first turn-on time is reached, the sound state changes from SNDS-OFF (sounds off) to sounds T-ON (sounds turn on), and new turn off and turn on times are generated randomly. As the system executes the sounds T-ON subroutine in the main loop, the volume of the sound increases by a given increment each second. The system then checks for whether the volume equals the target volume, which will differ depending on whether the cradle is operating in the day or night state. If the volume does not equal the target volume, the subroutine executes again. If the volume does equal the target volume, then the sound is as loud as targeted, and the sound state changes to SNDS-ON (sounds on). Of course, target sound volume may be set, or the sound profile scheme described above may be replaced, by a conventional manual volume control circuit.

In the SNDS-ON state, the system checks for whether the dwell is less than the maximum dwell. If the sound equals maximum dwell, the system remains in the SNDS-ON state and never turns off. If the dwell is less than maximum, the sound turns off when the real-time count of minutes equals the sound turn off time which was randomly set, as previously described. At that point, the sound state changes to sounds T-OFF (sounds turn off), and the sound decreases every second until the volume equals 0, at which point the system returns to the SNDS-OFF state.

FIGS. 10(f)–(g) show the motor state subroutines. The motor state subroutines operate independently from the sound state subroutines but are otherwise very similar. In the MOTS-OFF (motor off) state, the system determines whether dwell is greater than 0. If no, the motor remains off. If yes, the system checks whether the current real-time count of minutes is equal to the randomly-preset turn-on time. If no, it simply returns. If yes, it randomly sets new turn-off and turn-on times, sets the target speed based on whether the day-night state is day or night, and changes the motor state to MOTS-TON (motor turn on). The MOTS-TON routine checks whether the present speed equals the target speed. If yes, the system changes to the MOTS-ON (motor on) state, which checks whether the current time equals the randomly-set MOTS-TOFF (motor turn off) time. If no, the system returns and checks again the next time through. If yes, it sets the target speed to the stop seed, which is not quite off, and waits for the motion detector trip to go off. When that happens, the system changes states to MOTS-TOFF, which then seeks the motion interrupt in centering before shutting off completely. The MOTS-TOFF routine seeks speed equal to the target speed setting before stopping. Once the target speed is reached the first time, the routine seeks the motion interrupt count generated by the real-time count-interrupt routine.

Because the ramping for motor speed is faster than the ramping for sound volume, it is easiest to handle motor-speed transitions in the real-time count-interrupt routine. The motion detection interrupt routine, shown in FIG. 10(m), is very simple. Every time the motion detector trips or switches, it increments a byte in memory or register. The motor state processor detects that byte in memory as an indication that the motion detector has been tripped.

Figure 10K:
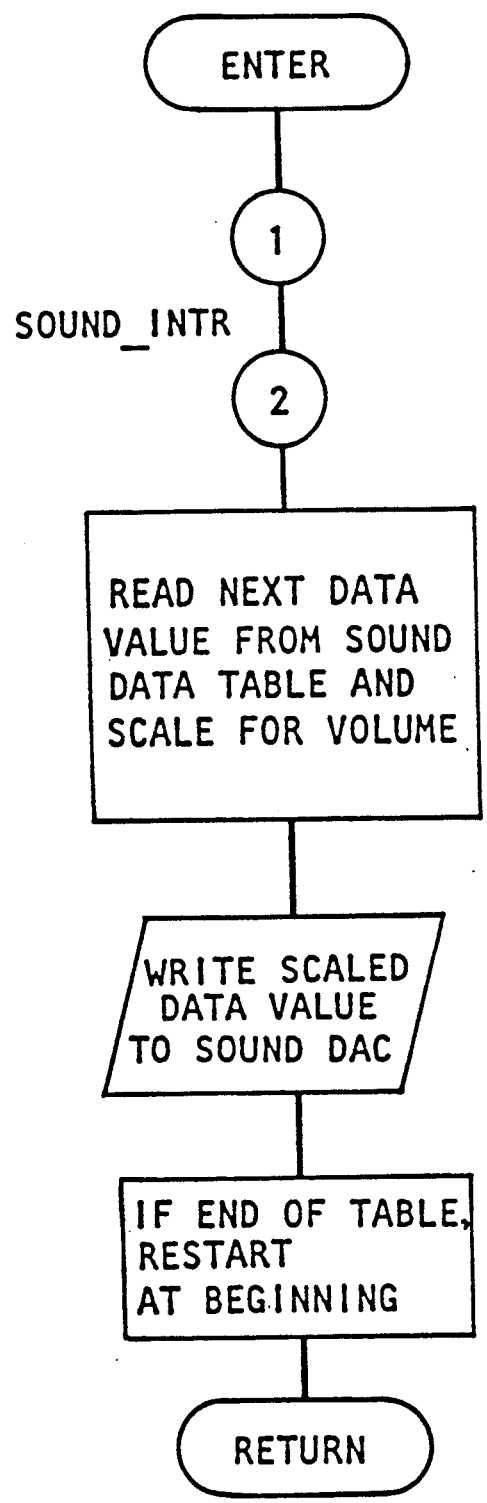
Figure 10M:
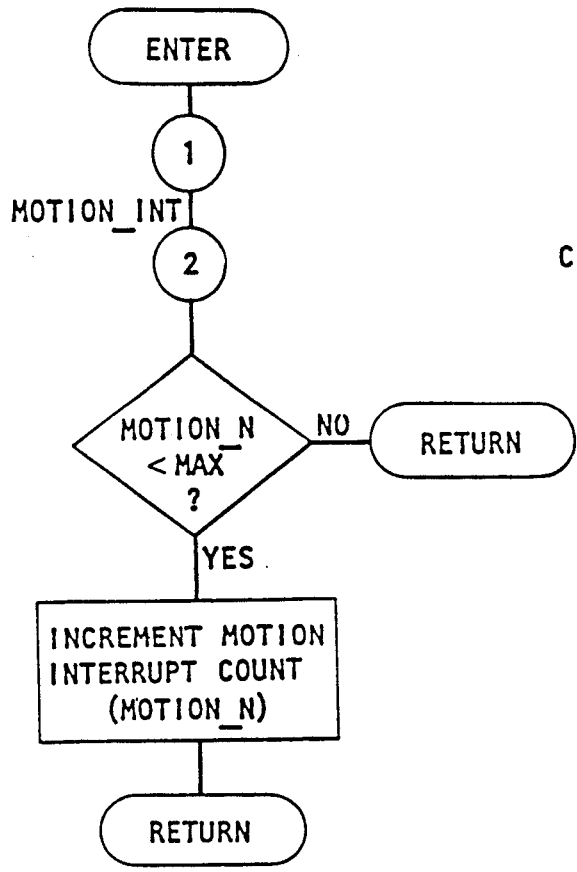
Figure 10L:
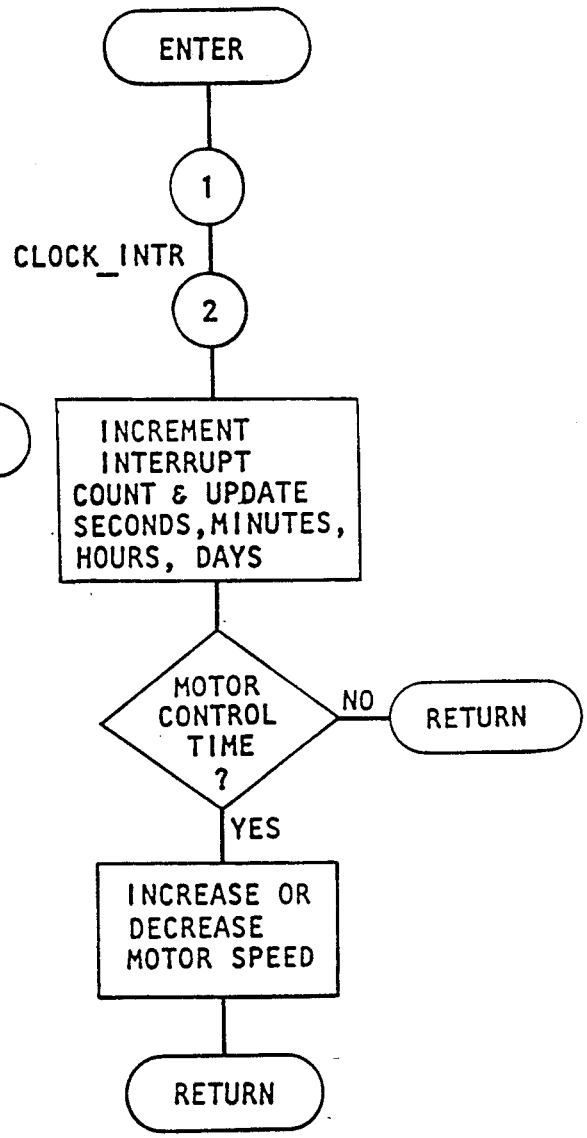

Each clock timer overflow results in a clock interrupt and execution of the motor-control interrupt routine, as shown in FIG. 10(l). The overflow is currently set for about every 50 milliseconds. The interrupt increments bytes in memory. One byte counts the 50 millisecond interrupts. Once the system accumulates 20 such interrupts, it updates the byte called "seconds." Once it accumulates 60 "seconds" it increments the byte called "minutes"; after accumulating 60 "minutes" it increments the byte called "hours"; after accumulating 24 "hours" it increments the byte called "days." The system also includes a byte called "10 days" (not presently used). After incrementing the real-time clock bytes as necessary, the system checks whether it is time to control the motor. If yes, then the system increases or decreases motor speed, depending on whether the motor state is MOTS-TON or MOTS-TOFF.

FIGS. 10(h)–(i) show the day-night state subroutines. The day-night state processor reads the output of solar sensor 4. If the output indicates light has been detected, it increments a byte called "day count"; otherwise it decrements day count. A day count reading of 5,000 indicates that the solar sensor 4 has detected light 5,000 times more often than it has detected no light. Similarly, a day count reading of −5,000 indicates that the solar sensor 4 has detected no light 5,000 times more often than it has detected light.

State DAYS-OFF is equivalent to nighttime. Once the day count reaches 5,000, which means light is detected much more frequently than no light, the system increments the motor dwell to the day dwell value. It also changes the state to DAYS-TON (days turn on), which increments the volume of the sound which includes heart sounds (the beat rate of which is also increased), and increments motor speeds every minute until they reach the preset daytime values. At that point, the system changes states to DAYS-ON (days on), where it continues to read the output from solar sensor 4 until it indicates it has seen no light 5,000 times more often than it has seen light. When that occurs, the system sets the motor dwell to the night dwell value and changes the state to DAYS-TOFF (days turn off). While in the DAYS-TOFF state, the system decreases the sound volume, heart-beat rate and motor speed until they reach their preset night values, in approximately 5 minutes. Finally, the system changes back to the DAYS-OFF (night) state. It should be noted that the solar sensor 4 is checked repeatedly to ensure against false "daytime" detection, for example, on sensing the transient condition of a lamp turned on briefly in the proximity of the cradle.

FIG. 10(j) shows the SLOW-STOP and CHECK-MOTOR subroutines. The system enters the SLOW-STOP subroutine from the main control program when stop/reset switch 6 is pressed. First, the subroutine increases the motor ramp rate so the motor turns off faster (though, not instantly) than it normally would. Second, it sets the motor target speed to the stopping speed used to check for centering of the cradle. Once the motor and sound are both off, the system jumps back to location 0, which is the reset position in FIG. 10(a). If either the motor or sound or both are still on, the system uses the MOT-TOFF and SNDS-TOFF routines to decrease the motor speed and sound volume and to center the cradle.

The check motor subroutine, which is ignored in test mode, is used to time out in the case where the no motion detector is seen. In normal cradle operation, where the motor speed is greater than 0 (i.e., the motor is actually on), the system checks to see if the motion end (the byte that is incremented when the motion detector trip interrupt is executed) is greater than 0. If yes, this indicates a trip and the system executes the TO-CHECK (time out check) routine to set a time value to indicate when in the future the system will time out. If the current seconds elapsed value from the real-time clock interrupt equals the time-out time, the system resets i.e., goes back to the reset location in FIG. 10(a), thus indicating that the system has timed out and stopped. If the current seconds elapsed value from the real-time clock interrupt does not equal the time-out time, the system returns and the routine will be ignored.

FIG. 10(k) shows the sound generation interrupt. The interrupt rate determines the heart rate. The sound interrupt reads the next data value from the sound data table and writes it to the sound DAC after scaling it to the current sound volume setting. When it reaches the end of the table, the system resets its pointer and restarts at the beginning.

The motion generation means, under the control of the previously-described electronic circuitry in module 28, operates within the following general parameters. The cradle motor 12, or cradle motors 41–44 and 45, depending on the embodiment, will be turned on and off randomly while the cradle 1 is in operation. The minimum on-time is about 5 minutes and maximum on-time is about 45 minutes. The gradual transition between on and off takes about 30 seconds. (The motor on-time is counted from when the motor first begins to turn on until it is completely off again.). The motor dwell declines linearly from about 50% at minimum age to 0% at maximum age. Of course, other time intervals and dwell ratios may also be used.

Similarly, the sound generation means operates within the following general parameters. The sound will be turned on and off randomly while the cradle 1 is in operation. The minimum on-time is about 5 minutes and the maximum on-time is about 45 minutes. The gradual transition between on and off takes about 30 seconds. (The sound on-time will be counted from when the sound first begins to turn on until it is completely off again.). The sound dwell declines linearly from about 100% at minimum age to 0% at maximum age. The simulated heart beat rate is about 80 beats per minute for daytime operation and about 62 beats per minute for nighttime operation to simulate typical active and at-rest heart rates. Of course, other rates may also be used, and the transition from day to night rates takes about 15 minutes.

Figure 11:
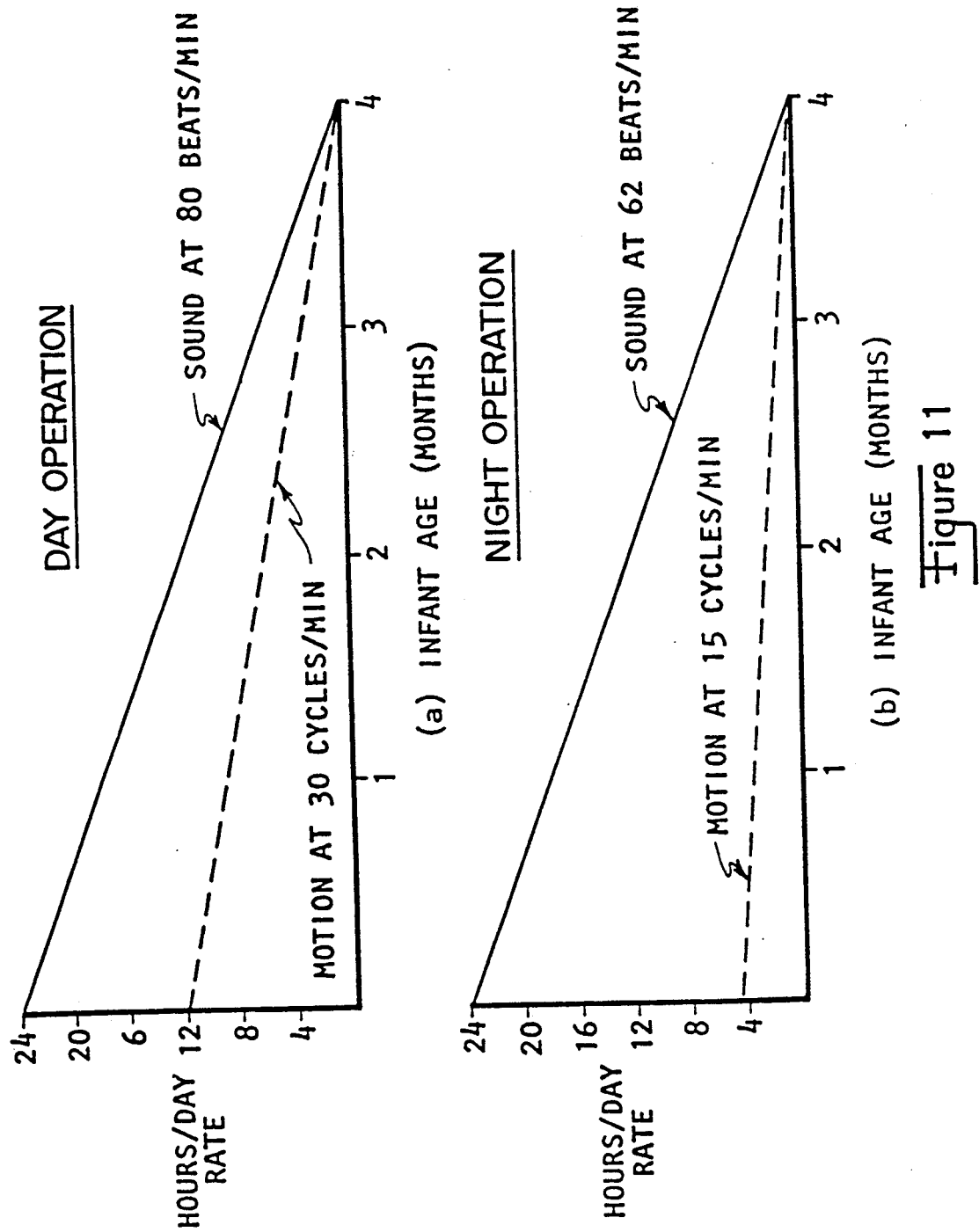
FIGS. 11 (a) and (b) are graphs which show changes in sound and motion as a function of infant age and time of day in the operation of an embodiment of the present invention.
Figure 12:
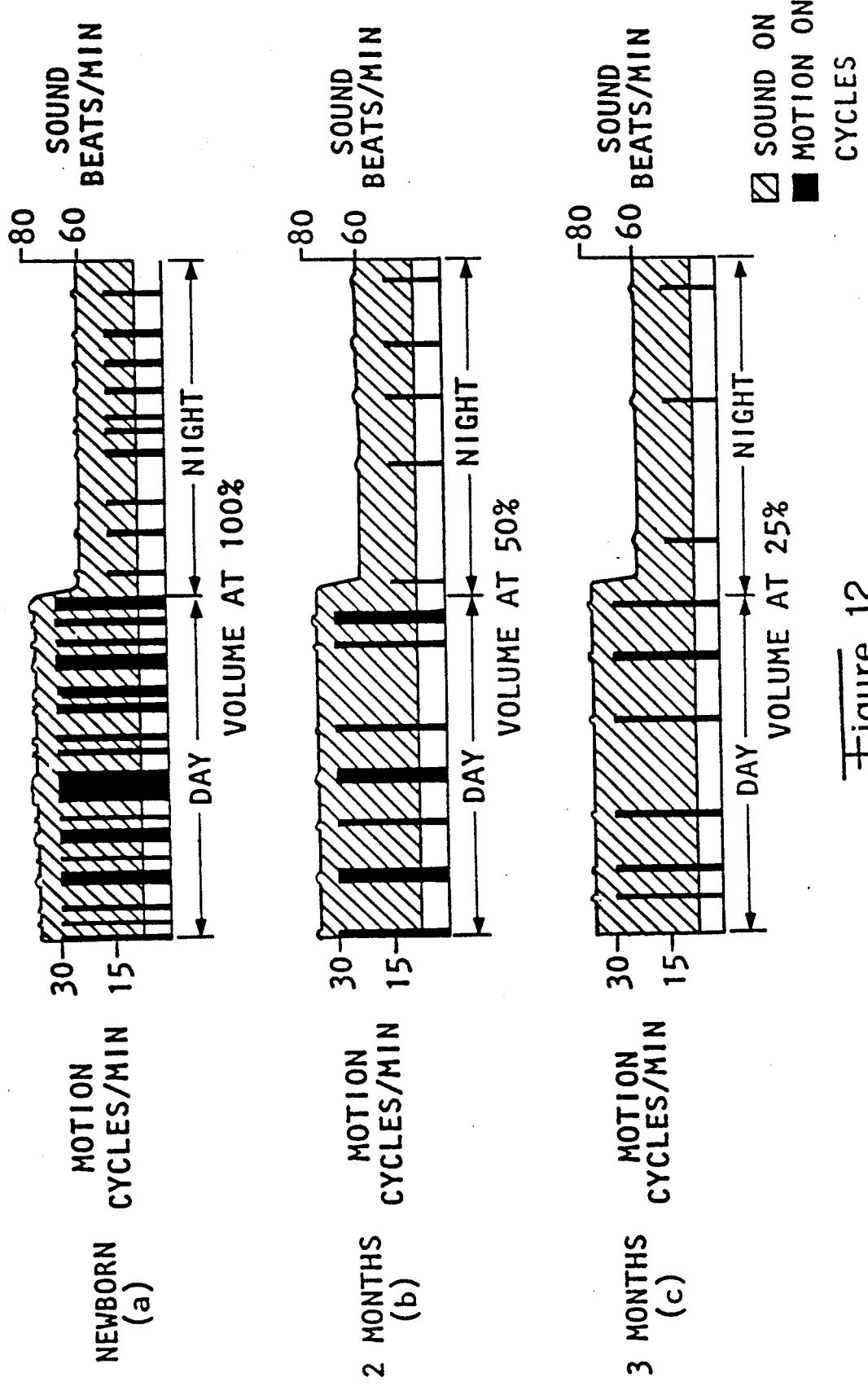
FIGS. 12 (a)–(c) are graphs which show characteristic 24-hour patterns of sound and motion for three infant age settings in accordance with an embodiment of the present invention.

The characteristic interrelationships among the parameters are graphically displayed in FIGS. 11 and 12.

FIGS. 11(a) and (b) show the gradual change in the duration and frequency of sound and motion as a function of infant age (from 0-4 months) for the day and night operational modes of the present invention. In general, the motion is faster and the heartbeat sound is faster and louder in the day mode than in the night mode. As the infant ages, the amount of time the motion and sound parameters are "ON" decreases gradually, but the rates of the motion and heartbeat sounds remain the same. At the end of the transition period, shown here as age 4 months, cradle motion and sounds cease completely.

FIGS. 12(a)-(c) show characteristic on-off and intensity cycles for a typical 24 hour period at infant age settings of newborn, 2 months and 3 months. The motion and sound both start when start switch 7 is pressed. Subsequently, however, the motion and sound on-off times may be randomized independently of each other (as illustrated in the left portion of FIG. 12(a)), or may track at least to the extent of the ramp up and down between a base level (day or night) and an elevated level representative of increased heart rate associated with movements (as illustrated in the remaining portions of FIGS. 12(a), (b) and (c)). The particular patterns shown in FIGS. 12(a)-(c), therefore, are representative only of typical random patterns and the decrease in the random activity with the age of the infant.

In addition to the patterns shown in FIGS. 11(a) and (b) and 12(a)-(c), and the general parameters described above, further alternatives exist for control of sound and motion in the present invention. These include (1) gradually reducing sound amplitude in a linear or non-linear fashion over the 4 month period rather than full on-off cycles; (2) gradually reducing the rate (cycles/minute) and/or amplitude (length of stroke) of motion, rather than on-off cycles; (3) varying the "normal" sound rate (80 beats/minute-day, 62 beats/minute-night) and "normal" motion rate (30 cycles/minute-day, 15 cycles/minutes-night) as a function of the mother's baseline heart rate; (4) varying the 4 month use period; and (5) varying sound and motion rates as a function of specific infant activities (e.g. pushing a lever).

Figure 13:
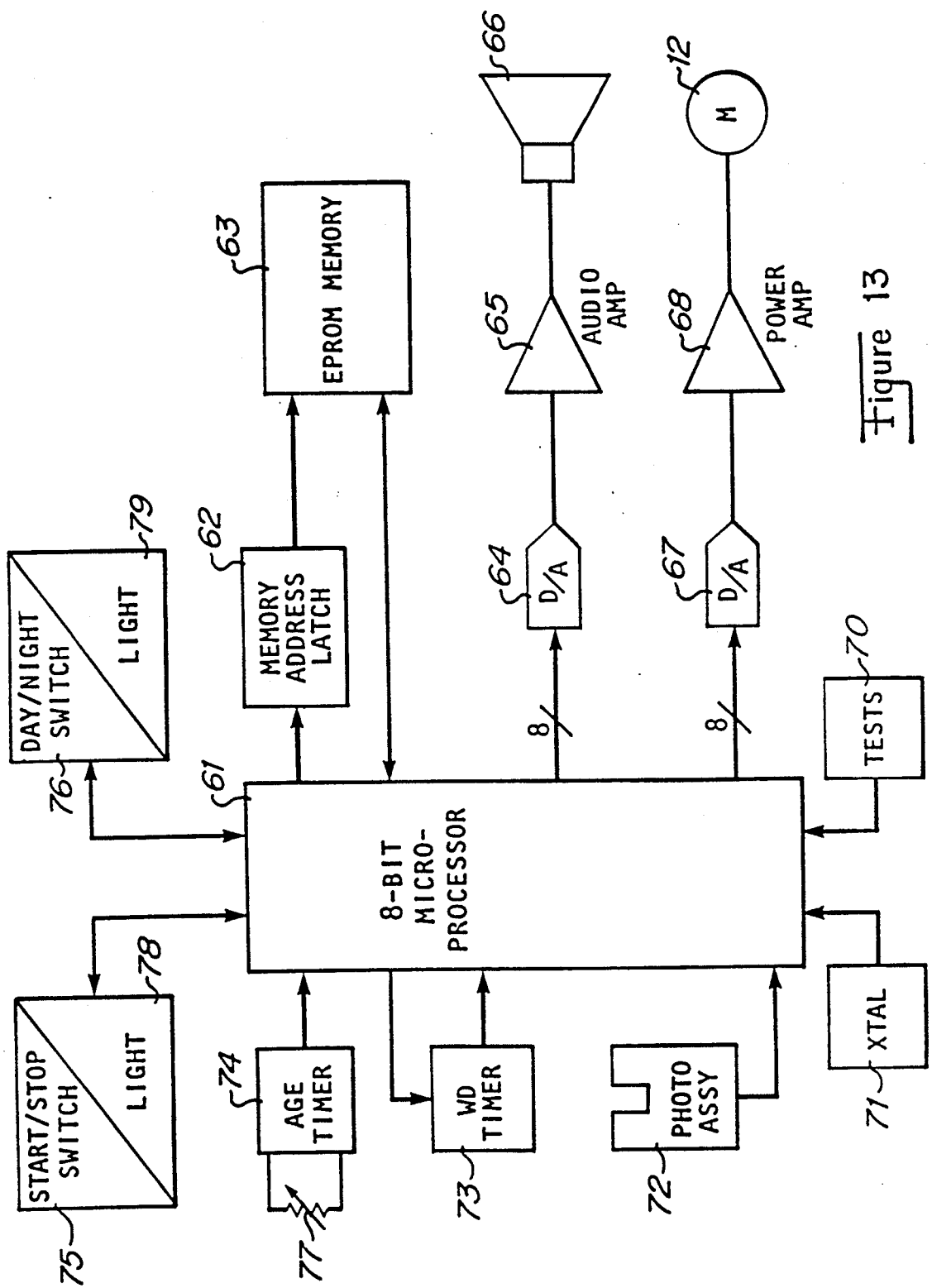
FIG. 13 is a block schematic diagram of one embodiment of the electronic controller of the present invention.

Referring now to the block schematic diagram of FIG. 13, there is shown the circuitry in one embodiment of the electronics module 28 including the microprocessor 61, the memory address latch 62, the EPROM memory 63, and the crystal clock 71 which control program execution. The primary outputs are sound through digital-to-analog converter 64 and amplifier 65 to speaker 66, and the motion of motor 12 that is powered by amplifier 68 and digital-to-analog converter 67. Of course, two such motor control circuits are included for separate motors or linear actuators such as actuators 41-44 and 45. The microprocessor 61 controls these outputs in conventional manner using 8-bit control words applied to the D/A converters 64, 67. The output from D/A converter 64 is supplied to audio amplifier 65 which drives the speaker 66. The motor 12 (or 41-44 and 45) is controlled through D/A converter 67 which receives an 8-bit control word from microprocessor 61 and which supplies output to power amplifier 68 that drives the motor.

The particular sound and sound pattern delivered by the speaker 66 are attributable to the sounds that are digitized and stored in EPROM memory 63, which sounds may be previously-recorded actual intrauterine sounds. The particular amounts of time that the sounds and the motor motions are in the on-states, and the amplitudes, and the durations controlled by algorithms stored in the memory 63.

In operation of the system, the algorithms, for controlling the amount of time for the sounds and the motor(s) to be in the on-states can be changed by an input provided through the age timer 74 and its associated slide potentiometer 9, 77. The slide potentiometer 9, 77 is located conveniently in the front control panel 8 of the cradle and is controlled by the user. Other inputs which the user may control include the start/stop switch 75 and day/night switch 76. Start/stop switch 75 controls the starting and the stopping of the system, and the day/night switch 76 determines whether the system, should be operating in the day mode or the night mode. Each of the switches 75, 76 includes an associated indicator light 78, 79. Thus, the light 78 associated with the start/stop switch 75 indicates whether the system is running or is in a stopping mode. When the system is running or is in the stopping mode, the indicator 78 flashes slowly, for example, at a one-second rate. When the system has stopped (and is therefore ready to start), the light 78 is continuously on. Indicator light 79 indicates operation of the system in the day mode when the light is off, and in the night mode when the light is on. In addition to the user controls and the outputs thus described, the system also includes a photo detector assembly 72 including optical transmitter and receiver which are positioned to monitor the cradle motion, for example, as represented by the rotation of one of the secondary gears driven by motor 12. Signals thus produced by the photo detector assembly 12 are continually supplied to the microprocessor 61 to generate an interrupt or other control signal in the microprocessor 61. If such control signal ceases to occur, a delay interval will time-out in the microprocessor 61 after which the microprocessor 61 will shut down the entire system by turning off power to the motor and turning off the sound as a safety response, for example, to the motor 12 stalling or to the belt driving one of the secondary gears breaking. An additional safety response is provided by watchdog timer 73 which functions to constantly monitor the proper operation of the program execution by the microprocessor 61. This watchdog timer 73 automatically turns off the microprocessor 61 if the watchdog timer 73 is not reset within a 2-second interval that is included in normal program-controlled operation of the microprocessor 61. Thus, in normal operation, the watchdog timer 73 will always be reset within the 2-second interval. However, if a power failure or low-voltage condition occurs that might cause the microprocessor 61 to deviate from normal program execution, then the watchdog timer 73 automatically stops the microprocessor 61 at the expiration of the 2-second interval. Various test switches 70 are provided as inputs for controlling the operation of the microprocessor 61 in different test modes to facilitate debugging during manufacturing and system testing doing field service.

It should be apparent from the foregoing that the preferred embodiments of the invention provide an apparatus and method which can initially simulate the environmental parameters of the near-term gravid uterus, particularly motion and sound, and can transition the infant from the simulated intrauterine environment to an extrauterine environment. Other embodiments of the present invention include a platform capable of imparting the above-described two-axis motion to an incubator for an infant, or other housing for an individual, that is supported on such platform. Also, the sound motion and sound profiles described above may be manually-controlled or continuous as desired for a particular infant or individual.

What is claimed is:

1. The method of providing a controlled environment for an individual within a housing, comprising the steps of:

supporting the housing for substantially only translational motion along a longitudinal axis thereof and for rotational movement about an axis substantially aligned with the longitudinal axis; and imparting translational motion to the housing substantially along the longitudinal axis and rotational motion about the axis substantially aligned with the longitudinal axis for approximating the motion experienced by a fetus while its mother is walking.

2. The method of claim 1, including the additional step of:

selectively modifying the motions imparted to an individual within the housing over a period of time.

3. The method according to claim 2 wherein the motion imparted to the housing varies within an operating interval, and varies over a plurality of operating intervals from an initial operating condition of motion imparted to the housing per unit time to an operating condition involving less motion imparted to the housing per unit time.

4. The method of claim 1, including the additional steps of:

positioning a sound transducer within the housing at a location therein providing support for an individual therein;

imparting to the individual, via the sound transducer, a selected sound profile; and selectively modifying the sound profile imparted to the individual over a period of time.

5. The method of claim 4, including the additional step of:

selectively modifying both the motion and the sound profile imparted to the individual simultaneously.

6. The method of claim 5 wherein the motion and sound profile are selectively modified under control of an individual within the housing.

7. The method of claim 5 wherein the sound imparted to an individual includes impulses resembling heart rate at a selected repetition rate, and in the step of selectively modifying, the repetition rate of impulses varies in relation to motion imparted to the individual.

8. The method according to claim 1 wherein the translational and rotational motions are imparted to the housing at relatively different rates to approximate the motion experienced by a fetus while its mother is walking.

9. The method according to claim 1 wherein an individual is oriented within the housing in substantial alignment with the longitudinal axis.

* * * * *